US008633034B2

(12) United States Patent
Trotter et al.

(10) Patent No.: US 8,633,034 B2
(45) Date of Patent: Jan. 21, 2014

(54) METHODS FOR EVALUATING THE AGGREGATION OF A PROTEIN IN A SUSPENSION INCLUDING ORGANOPOLYSILOXANE AND MEDICAL ARTICLES COATED WITH ORGANOPOLYSILOXANE CONTAINING A PROTEIN SOLUTION

(75) Inventors: Joseph T. Trotter, La Jolla, CA (US); Jean-Bernard Hamel, Saint Cassien (FR); John Frank Carpenter, Littleton, CO (US); Theodore Randolph, Niwot, CO (US); John Paul Gabrielson, Longmont, CO (US)

(73) Assignees: Becton, Dickinson and Company, Franklin Lakes, NJ (US); The Regents of the University of Colorado, Denver, CO (US)

( * ) Notice: Subject to any disclaimer, the term of this patent is extended or adjusted under 35 U.S.C. 154(b) by 191 days.

(21) Appl. No.: 12/739,009

(22) PCT Filed: Oct. 22, 2008

(86) PCT No.: PCT/US2008/080721
§ 371 (c)(1),
(2), (4) Date: Jan. 14, 2011

(87) PCT Pub. No.: WO2009/055427
PCT Pub. Date: Apr. 30, 2009

(65) Prior Publication Data
US 2011/0106044 A1 May 5, 2011

Related U.S. Application Data

(63) Continuation-in-part of application No. PCT/US2008/068136, filed on Jun. 25, 2008.

(60) Provisional application No. 60/999,920, filed on Oct. 22, 2007, provisional application No. 60/937,179, filed on Jun. 25, 2007.

(51) Int. Cl.
*G01N 33/533* (2006.01)
*G01N 31/00* (2006.01)
*G01N 33/00* (2006.01)

(52) U.S. Cl.
USPC .................. 436/546; 436/4; 436/86; 436/539

(58) Field of Classification Search
USPC ........................................ 436/546, 4, 86, 539
See application file for complete search history.

(56) References Cited

U.S. PATENT DOCUMENTS

| 4,959,402 A | 9/1990 | Williams et al. |
| 4,994,552 A | 2/1991 | Williams et al. |

(Continued)

FOREIGN PATENT DOCUMENTS

| EP | 0982041 A | 3/2000 |
| EP | 1811297 A | 7/2007 |

(Continued)

OTHER PUBLICATIONS

Gabrielson, J. et al. "Silicone oil contamination of therapeutic protein formulations: Surfactant and protein effects", 234th ACS National Meeting (Aug. 2007) BIOT-227.*

(Continued)

*Primary Examiner* — Shafiqul Haq
*Assistant Examiner* — Gary E Hollinden
(74) *Attorney, Agent, or Firm* — The Webb Law Firm

(57) ABSTRACT

This invention relates to methods for evaluating or inhibiting the aggregation of a protein in an aqueous suspension including organopolysiloxane and medical articles coated with organopolysiloxane containing a protein solution including sugar and a non-ionic surfactant.

19 Claims, 16 Drawing Sheets

(56) References Cited

U.S. PATENT DOCUMENTS

| | | | |
|---|---|---|---|
| 5,034,482 | A | 7/1991 | Kohara et al. |
| 5,540,494 | A | 7/1996 | Purvis, Jr. et al. |
| 5,599,882 | A | 2/1997 | Nishi et al. |
| 5,610,253 | A | 3/1997 | Hatke et al. |
| 5,623,039 | A | 4/1997 | Hatke et al. |
| 5,650,471 | A | 7/1997 | Abe et al. |
| 5,854,349 | A | 12/1998 | Abe et al. |
| 5,856,414 | A | 1/1999 | Hatke et al. |
| 5,866,662 | A | 2/1999 | Hatke et al. |
| 6,005,113 | A | 12/1999 | Wu et al. |
| 6,063,886 | A | 5/2000 | Yamaguchi et al. |
| 6,461,334 | B1 | 10/2002 | Buch-Rasmussen et al. |
| 6,486,264 | B1 | 11/2002 | Tsunogae et al. |
| 6,511,756 | B1 | 1/2003 | Obuchi et al. |
| 6,525,084 | B2 | 2/2003 | Rasmussen et al. |
| 6,525,144 | B1 | 2/2003 | Tanahashi et al. |
| 6,638,519 | B1 | 10/2003 | Lorant |
| 6,653,424 | B1 | 11/2003 | Sakamoto et al. |
| 6,908,970 | B2 | 6/2005 | Tsunogae et al. |
| 6,951,898 | B2 | 10/2005 | Hammond et al. |
| 6,995,226 | B2 | 2/2006 | Taguchi et al. |
| 7,026,401 | B1 | 4/2006 | Osan et al. |
| 7,037,993 | B2 | 5/2006 | Taguchi et al. |
| 8,030,095 | B2 * | 10/2011 | Harriman ............... 436/535 |
| 8,354,239 | B2 * | 1/2013 | Gaylord et al. ............ 435/7.1 |
| 2002/0037401 | A1 | 3/2002 | Buch-Rasmussen et al. |
| 2003/0072807 | A1 | 4/2003 | Wong et al. |
| 2005/0053598 | A1 | 3/2005 | Burke et al. |
| 2005/0065192 | A1 | 3/2005 | Yednock et al. |
| 2005/0069935 | A1 * | 3/2005 | Boehm et al. ............ 435/6 |
| 2005/0074451 | A1 | 4/2005 | Yednock et al. |
| 2005/0123947 | A1 | 6/2005 | Quake et al. |
| 2006/0051353 | A1 | 3/2006 | Colombel et al. |
| 2009/0111768 | A1 * | 4/2009 | Caldwell et al. ............ 514/44 |
| 2010/0255477 | A1 * | 10/2010 | Bazan et al. ............ 435/6 |
| 2011/0106044 | A1 * | 5/2011 | Trotter et al. ............ 604/403 |

FOREIGN PATENT DOCUMENTS

| | | | |
|---|---|---|---|
| JP | 57106622 | A | 7/1982 |
| JP | 63264626 | A | 11/1988 |
| JP | 1158029 | A | 6/1989 |
| JP | 3115338 | A | 5/1991 |
| JP | 3121122 | A | 5/1991 |
| JP | 8100029 | A | 4/1996 |
| JP | 8109222 | A | 4/1996 |
| JP | 8183812 | A | 7/1996 |
| JP | 8231652 | A | 9/1996 |
| JP | 10287713 | A | 10/1998 |
| JP | 11218601 | A | 8/1999 |
| JP | 2003504443 | A | 2/2003 |
| JP | 2003513294 | A | 4/2003 |
| JP | 2007536555 | A | 12/2007 |
| JP | 4174968 | B2 | 8/2008 |
| JP | 4557124 | B2 | 7/2010 |
| JP | 4691867 | B2 | 3/2011 |
| WO | 9717610 | A | 5/1997 |
| WO | 9944754 | A | 9/1999 |
| WO | 9944755 | A | 9/1999 |
| WO | 03007868 | A | 1/2003 |
| WO | 2007082757 | A2 | 7/2007 |
| WO | 2008/072503 | A1 | 6/2008 |
| WO | 2009003010 | A2 | 12/2008 |

OTHER PUBLICATIONS

Latoya S. Jones et al., "Silicone Oil Induced Aggregation of Proteins," Journal of Pharmaceutical Sciences, Apr. 2005, pp. 918-927, vol. 94, No. 4.

Danny K. Chou et al., "Effects of Tween 20® and Tween 80® on the Stability of Albutropin During Agitation," Journal of Pharmaceutical Sciences, Jun. 2005, pp. 1368-1381, vol. 94, No. 6.

Eva Y. Chi et al., "Roles of conformational stability and colloidal stability in the aggregation of recombinant human gramulocyte colony-stimulating factor," Protein Science, 2003, pp. 903-913, vol. 12.

Eva Y. Chi et al., "Physical Stability of Proteins in Aqueous Solution: Mechanism and Driving Forces in Nonnative Protein Aggregation," Pharmaceutical Research, Sep. 2003, pp. 1325-1336, vol. 20, No. 9.

Eva Y. Chi et al., "Heterogeneous Nucleation-Controlled Particulate Formation of Recombinant Human Platelet-Activating Factor Acetylhydrolase in Pharmaceutical Formulation," Journal of Pharmaceutical Sciences, Feb. 2005, pp. 256-274, vol. 94, No. 2.

Aiqian Ye et al., "Influence of Polysaccharides on the Rate of Coalescence in Oil-in-Water Emulsions Formed with Highly Hydrolyzed Whey Proteins," Journal of Agricultural and Food Chemistry, 2004, pp. 5491-5498, vol. 52.

Yong-Sung Kim et al. "Thermodynamic Modulation of Light Chain Amyloid Fibril Formation," The Journal of Biological Chemistry, Jan. 21, 2000, pp. 1570-1574, vol. 275, No. 3.

Yong-Sung Kim et al. "Counteracting Effects of Renal Solutes on Amyloid Fibril Formation by Immunoglobulin Light Chains," The Journal of Biological Chemistry, Jan. 12, 2001, pp. 1626-1633, vol. 276, No. 2.

Sampathkumar Krishnan et al., "Aggregation of Granulocyte Colony Stimulating Factor under Physiological Conditions: Characterization and Thermodynamic Inhibition," Biochemistry, 2002, pp. 6422-6431, vol. 41.

Ye Zhang et al., "Mechanism for Benzyl Alcohol-Induced Aggregation of Recombinant Human Interleukin-1 Receptor Antagonist in Aqueous Solution," Journal of Pharmaceutical Sciences, Dec. 2004, pp. 3076-3089, vol. 93, No. 12.

Tsutomu Arakawa et al., "Factors Affecting Short-Term and Long-Term Stabilities of Proteins," Advanced Drug Delivery Reviews, 1993, pp. 1-28, vol. 10.

R. N. Baldwin, "Contamination of Insulin by Silicone Oil: a Potential Hazard of Plastic Insulin Syringes," Diabetic Medicine, 1988, pp. 789-790, vol. 5.

Richard K. Bernstein, MD, "Clouding and Deactivation of Clear (Regular) Human Insulin: Association With Silicone Oil From Disposable Syringes?," Diabetes Care, Nov.-Dec. 1987, pp. 786-787, vol. 10, No. 6.

E. Chantelau, "Silicone oil contamination of insulin," Diabetic Medicine, 1989, p. 278, vol. 6, Issue: 3.

E. Chantelau et al., "Silicone Oil Released From Disposable Insulin Syringes," Diabetes Care, Nov.-Dec. 1986, pp. 672-673, vol. 9, No. 6.

Ernst A. Chantelau et al., "Pollution of Insulin with Silicone Oil, a Hazard of Disposable Plastic Syringes," The Lancet, Jun. 22, 1985, p. 1459.

R. M. P. Doornbos et al., "Lissajous-Like Patterns in Scatter Plots of Calibration Beads," Cytometry, 1994, pp. 236-242, vol. 16.

Suzanne Hermeling et al., "Structure-Immunogenicity Relationships of Therapeutic Proteins," Pharmaceutical Research, Jun. 2004, pp. 897-903, vol. 21, No. 6.

Guy Furness (Editor), "Prefilled Syringes Innovations That Meet the Growing Demand," ONdrugDelivery Ltd, 2005, 28 pages, West Sussex, United Kingdom.

H. Schellekens, "When biotech proteins go off-patent.," Trends in Biotechnology, Aug. 2004, pp. 406-410, vol. 22, No. 8.

Wei Wang et al., "Antibody Structure, Instability, and Formulation," Journal of Pharmaceutical Sciences, Jan. 2007, pp. 1-26, vol. 96, No. 1.

J. H. Jett et al., "Quantitation of Cell Surface Antigen Density by Flow Cytometry," 4th Annual Symposium of Flow Cytometry, Voss, Norway, Jun. 4, 1979, published Jan. 1, 1979, Abstract.

* cited by examiner

Effect of Oil Viscosity on Oil Loading in Suspension

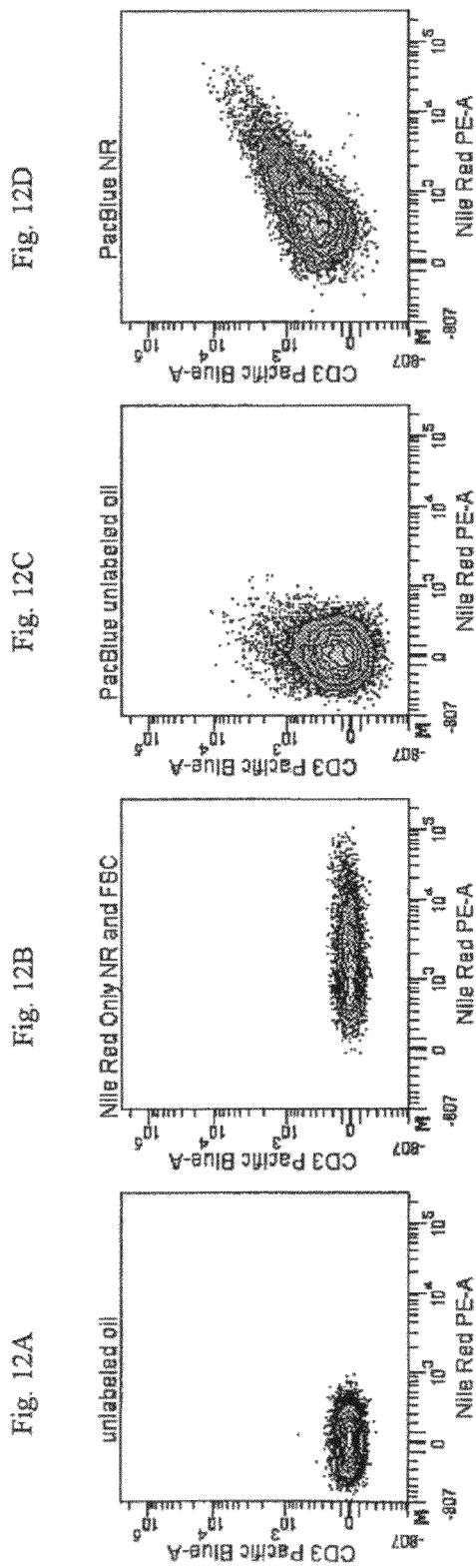

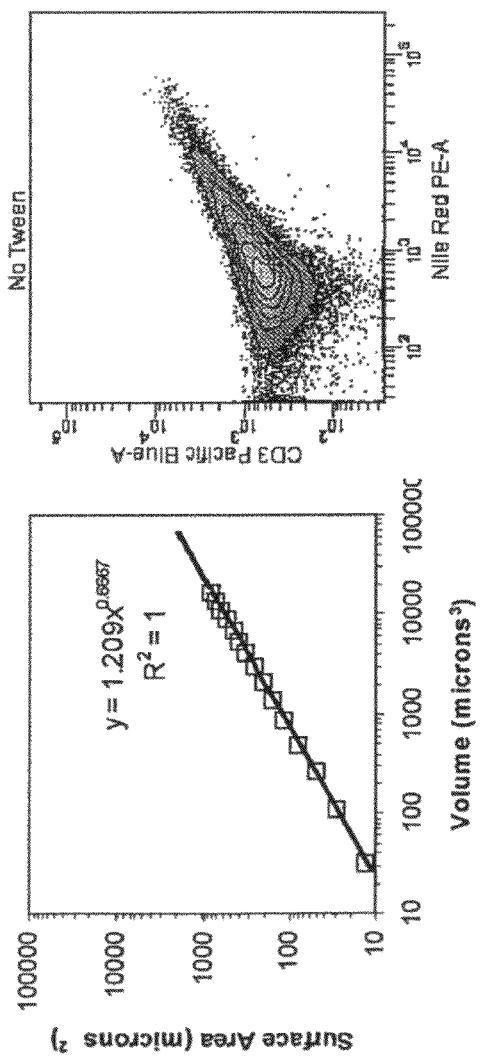

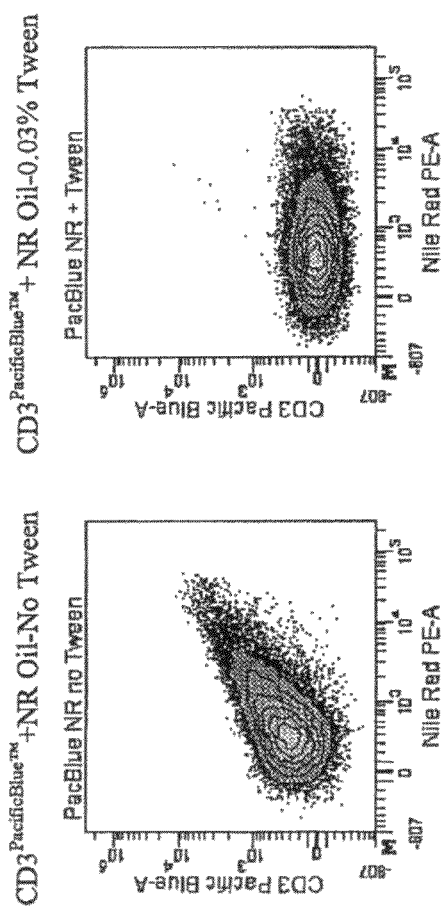

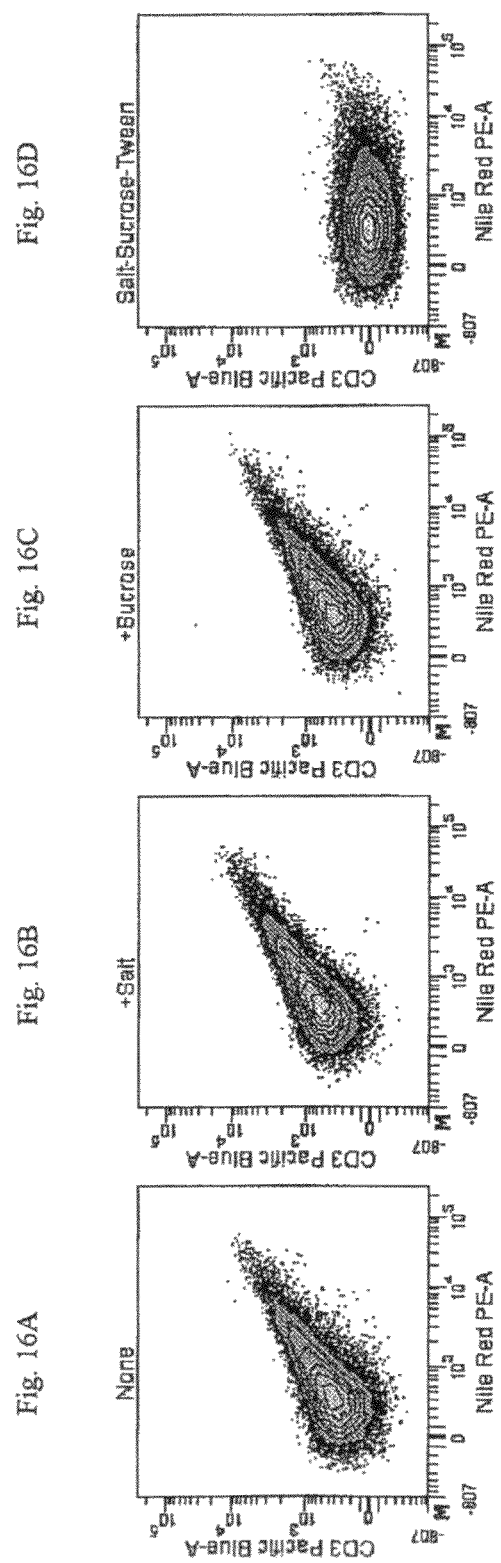

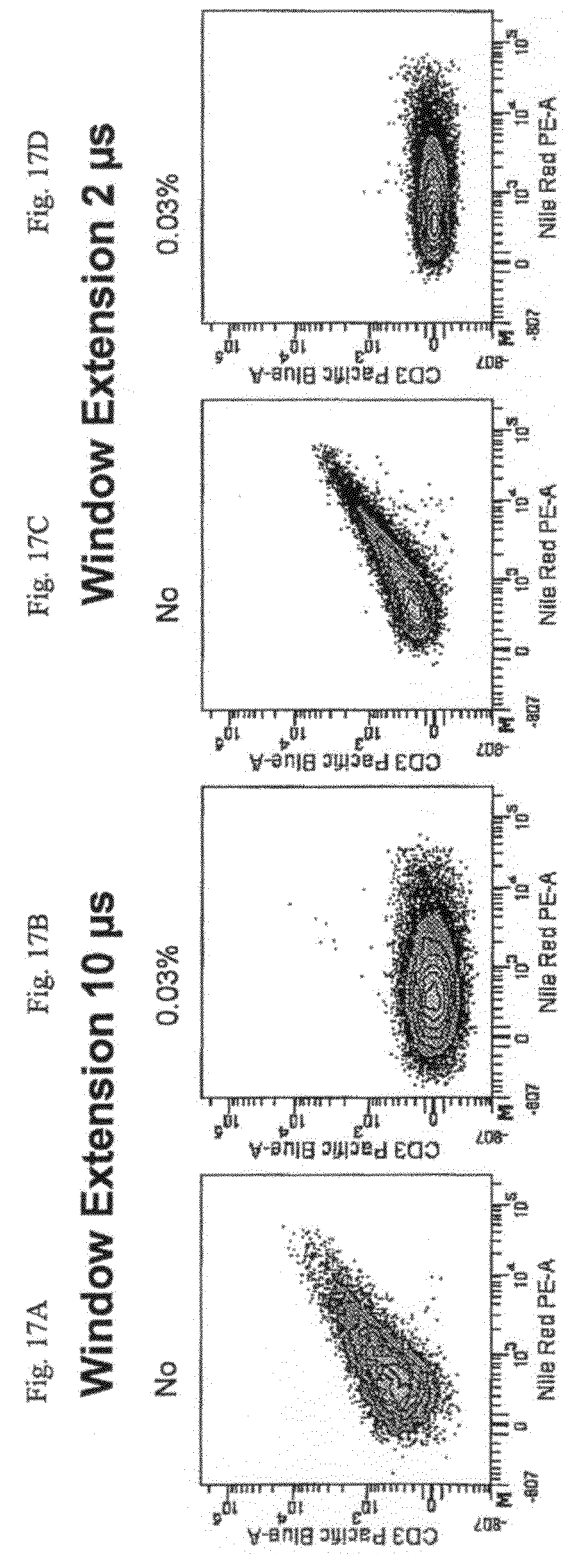

METHODS FOR EVALUATING THE AGGREGATION OF A PROTEIN IN A SUSPENSION INCLUDING ORGANOPOLYSILOXANE AND MEDICAL ARTICLES COATED WITH ORGANOPOLYSILOXANE CONTAINING A PROTEIN SOLUTION

CROSS-REFERENCE TO RELATED APPLICATION

This application claims the benefit of U.S. Provisional Patent Application Ser. No. 60/999,920, filed on Oct. 22, 2007, incorporated by reference herein in its entirety. This application also claims the benefit of PCT/US2008/068136 filed on Jun. 25, 2008, which claims the benefit of U.S. Provisional Patent Application Ser. No. 60/937,179, filed on Jun. 25, 2007, both incorporated by reference herein in their entireties.

BACKGROUND OF THE INVENTION

1. Field of the Invention

This invention relates to methods for evaluating the aggregation of a proteinaceous material in a suspension comprising an organopolysiloxane and medical components having surfaces coated with organopolysiloxane(s) and containing suspensions of proteinaceous materials.

2. Description of Related Art

Therapeutic proteins provide numerous unique and critical treatments for diseases and conditions, such as diabetes, cancer, hemophilia, rheumatoid arthritis, multiple sclerosis and myocardial infarction. There are already dozens of protein products on the market and hundreds more are in preclinical and clinical development. Furthermore, with the recent advent of robust methods for "humanizing" antibodies, there has been a new resurgence in biotechnology product development due to the tremendous increase in the number of antibody products being investigated for treatments of human disease. With modem genomic and proteomic approaches, new, safer and more effective protein therapeutics are being discovered daily. However, if a protein product cannot be stabilized adequately, its benefit to human health will never be realized. The shelf life required for economic viability of a typical protein pharmaceutical product is 18-24 months. Achieving this goal is particularly difficult because of the relatively low thermodynamic stability of the protein in its native state. The activity of a protein depends on its native, three-dimensional structure. In addition, proteins are highly susceptible to the formation of non-native aggregates and precipitates, even under conditions that thermodynamically greatly favor the native state over the unfolded state (e.g., neutral pH at 37° C.). The biological activity of a protein in an aggregate is usually greatly reduced. More importantly, non-native protein aggregates can cause adverse reactions in patients, such as immune response or anaphylactic shock. The capacity of aggregates of a given protein to induce adverse responses cannot be predicted; nor can the maximal level of aggregates required for safety be determined without costly and time-consuming clinical trials.

Thus, a major goal of formulation science is to design a formulation in which aggregation is kept to an extremely low level. Generally, the goal is to have no more than 1-2% of the entire protein population form aggregates over the shelf life of the product. Even under solution conditions where protein physical stability appears to be optimized so as to minimize protein aggregation in the bulk solution, there can be formation of visible and subvisible protein particles that may constitute only a minute fraction of the total protein population. The presence of even a small number of protein particles can render a product clinically unacceptable. Protein particulates are particularly immunogenic. Although particulates are desirable for vaccine formulations (where protein molecules are bound to aluminum salt particles), in a therapeutic protein product, the immune response to such particles can cause severe adverse responses in patients. Thus, even though the mass of protein that aggregates can be so small as to have essentially no deleterious effect on product potency, safety can be greatly compromised.

Particle formation can occur routinely during processing steps such as pumping of protein solution during vial/syringe filling. In other cases, particle formation may appear to be random. For example, particles may be seen in a small fraction of vials or prefilled syringes in a given product lot. Other times, a product filled into a given lot of vials or syringes may form protein particles in a large fraction of the containers. Unfortunately, these particles appear downstream of sterile filtration steps and cannot be removed by filtration during subcutaneous, intradermal, or intramuscular injection.

Silicone oils are commonly used as lubricants in medical articles. While silicone oils are not subject to oxidation, migration and stick could occur for pre-filled syringes, and high breakout and/or breakloose forces are a problem. Silicone oil has been shown under certain conditions, even at low concentrations, to induce protein aggregation. Several newly commercialized aqueous protein products, including erythropoietins (e.g., Recormon™ and Eprex™), interferons (e.g., Avonex™ and Rebif™) and rheumatoid arthritis therapies (e.g., Enbrel™ and Humira™) are manufactured in prefilled syringes. Inner surfaces of prefilled syringes are coated with silicone oil to enhance syringe functionality, and consequently, formulated protein is exposed to silicone oil surfaces. Silicone oil induced therapeutic protein aggregation is a concern in the pharmaceutical industry, potentially leading to loss of product and increased manufacturing costs.

There is a need for methods to assess aqueous suspensions or emulsions having proteinaceous materials to determine appropriate aggregation inhibitors to include in the solution to inhibit aggregation. The results of these investigations will provide the understanding needed for advising companies on how to develop protein formulations that are resistant to silicone oil-induced protein aggregation. In addition, an experimental system that allows rapid formulation screening is desirable. Thus, pharmaceutical and biotechnology companies can follow a rational formulation development plan to quickly optimal formulations for each protein that avoid the problem of silicone oil-induced protein aggregation and the potential adverse responses in patients. Model proteins and appropriate solution conditions can be determined that can be used for testing new syringes or medical articles in development.

SUMMARY OF THE INVENTION

In some non-limiting embodiments, the present invention provides methods for evaluating the aggregation of a proteinaceous material in a suspension comprising an organopolysiloxane, comprising: (a) providing an aqueous suspension of a fluorescently-labeled organopolysiloxane and a fluorescently-labeled proteinaceous material; (b) measuring relative particle fluorescence intensity of the fluorescently-labeled organopolysiloxane and the fluorescently-labeled proteinaceous material using fluorescence-activated particle sorting; and (c) comparing the relative intensity of the fluorescently-labeled organopolysiloxane to the relative intensity of the fluorescently-labeled proteinaceous material.

In some non-limiting embodiments, the present invention provides methods for evaluating the aggregation of a proteinaceous material in a suspension comprising an organopolysiloxane, comprising: (a) providing an aqueous suspension of a fluorescently-labeled organopolysiloxane and a fluorescently-labeled proteinaceous material, wherein the organopolysiloxane is labeled with a first fluorescent moiety which emits light within a first range of wavelengths and the proteinaceous material is labeled with a second fluorescent moiety which emits light within a second range of wavelengths when the fluorescent-labeled organopolysiloxane and the fluorescent-labeled proteinaceous material are each exposed to light of the same wavelength emitted by a laser, wherein the first range of wavelengths is substantially free of overlap with the second range of wavelengths; (b) measuring relative particle fluorescence intensity of the fluorescently-labeled organopolysiloxane and the fluorescently-labeled proteinaceous material using fluorescence-activated particle sorting; and (c) comparing the relative intensity of the fluorescently-labeled organopolysiloxane to the relative intensity of the fluorescently-labeled proteinaceous material.

In some non-limiting embodiments, the present invention provides methods for inhibiting the aggregation of a proteinaceous material in a suspension comprising an organopolysiloxane, comprising: (a) providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein (i) the at least one aggregation inhibitor is different in each aqueous suspension, or (ii) the amount of aggregation inhibitor is different in each aqueous suspension; (b) measuring relative particle fluorescence intensity of the fluorescently-labeled organopolysiloxane and the fluorescently-labeled proteinaceous material in each aqueous suspension using fluorescence-activated particle sorting; (c) comparing the relative intensity of the fluorescently-labeled organopolysiloxane to the relative intensity of the fluorescently-labeled proteinaceous material for each aqueous suspension; and (d) selecting at least one aggregation inhibitor for use in a suspension comprising a proteinaceous material based upon the comparison of the relative intensity of the fluorescently-labeled organopolysiloxane to the relative intensity of the fluorescently-labeled proteinaceous material for each aqueous suspension.

In some non-limiting embodiments, the present invention provides medical articles comprising: (a) a container comprising a chamber for receiving a solution, wherein the inner surface of the chamber has a coating thereon prepared from a composition comprising an organopolysiloxane; and (b) a solution comprising: (i) at least one proteinaceous material; (ii) at least one non-ionic surfactant; and (iii) at least one sugar.

In some non-limiting embodiments, the present invention provides medical articles comprising: (a) a container comprising a chamber for receiving a solution, wherein the inner surface of the chamber has a coating thereon prepared from a composition comprising an organopolysiloxane; and (b) a solution comprising: (i) at least one proteinaceous material; and (ii) at least one non-ionic surfactant.

BRIEF DESCRIPTION OF THE DRAWINGS

The present invention will best be understood from the following description of specific embodiments when read in connection with the accompanying drawings:

FIG. 12A is a plot of relative fluorescence intensity of CD3 antibody labeled with Pacific Blue™ dye (y-axis) versus relative fluorescence intensity of Nile Red labeled silicone oil (x-axis) for a sample of unlabeled silicone oil;

FIG. 12B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye;

FIG. 12C is a plot of relative fluorescence intensity of CD3 antibody labeled with Pacific Blue™ dye (y-axis) versus relative fluorescence intensity of Nile Red labeled silicone oil (x-axis) for a sample of CD3 antibody labeled with Pacific Blue™ dye;

FIG. 12D is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention;

FIG. 13A is a plot of theoretical particle surface area as a function of particle volume for a size range of perfect spheres;

FIG. 13B is a plot of particle surface area as a function of particle volume for a sample of silicone oil labeled with Nile Red dye and CD3 antibody labeled with Pacific Blue™ dye according to the present invention;

FIG. 14A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention;

FIG. 14B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant according to the present invention;

FIG. 16A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention;

FIG. 16B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 150 mM Salt according to the present invention;

FIG. 16C is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.5 M sucrose according to the present invention;

FIG. 16D is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, 0.5 M sucrose, 150 mM Salt, and 0.03% Tween 20® polyoxyethylene 20 sorbitan monolaurate non-ionic surfactant according to the present invention;

FIG. 17A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye measured at a window extension of 10 µs according to the present invention;

FIG. 17B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant measured at a window extension of 10 µs according to the present invention;

FIG. 17C is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye measured at a window extension of 2 µs according to the present invention; and FIG. 17D is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant measured at a window extension of 2 µs according to the present invention.

DETAILED DESCRIPTION

Figure 1A:
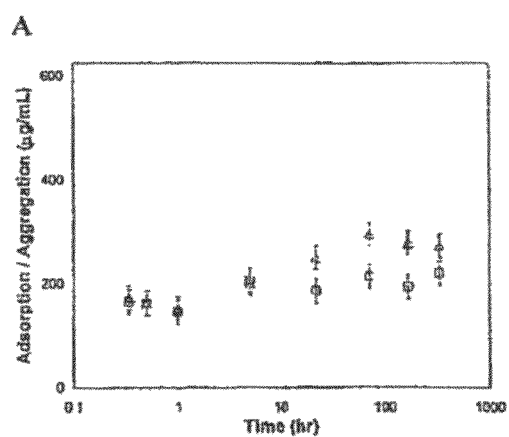
FIG. 1A is a plot of adsorption/aggregation of mAb with silicone oil as a function of time for a formulation including sucrose, mAb and silicone oil and a formulation including mAb and silicone oil.

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

While not intending to be bound by any theory, protein particle formation can arise from heterogeneous nucleation of protein aggregates on the surfaces of nanoparticles and microparticles of foreign materials. These particulate contaminants can include metals or silicone shed from vial filling pumps, tungsten microparticles produced during manufacture of glass syringes, and glass nanoparticles shed as a result of high-temperature depyrogenation procedures. In some non-limiting embodiments, the methods of the present invention can be useful in connection with preparation of prefilled syringes in which the surfaces are coated with silicone oil(s) or organopolysiloxane(s). Silicone oil is desirable to assure smooth, free travel of the stopper through the barrel of the syringe as the product is injected. The formation of protein particles in silicone oil-treated prefilled syringes, which can be nucleated by microdroplets of silicone oil, also can be of concern. Although such particles—and the protein aggregates that may result from them—are ubiquitous, virtually no systematic characterization of the problem and the mechanisms governing it have been addressed in the literature. Without such insight, industry will continue to be plagued with protein aggregation events and the resulting loss of product, increased costs, and safety risks to patients.

Homogeneous protein aggregation can be inhibited by using thermodynamic stabilizers (e.g., sucrose) that shift the native state ensemble away from structurally expanded conformations and toward the structurally most compact species. Stabilizers such as sucrose increase protein thermodynamic stability because they are preferentially excluded from the surface of protein molecules. Concomitant with preferential exclusion is an increase in protein chemical potential. The magnitudes of these two effects is directly proportional to the surface area of the protein exposed to solvent and are independent of the chemical properties of the side chains of exposed residues. Preferentially excluded solutes increase the free energy barrier between the most compact native state and the fully unfolded state or structurally expanded species within the native state ensemble, because the latter have a greater surface area and, hence, greater increase in chemical potential. Thus, sucrose shifts the equilibrium away from structurally expanded, aggregation-competent species.

In addition to thermodynamic modulation of species distribution within the protein molecular population, the energetics of protein-protein interactions in solution are important determinants of the kinetics of protein aggregation. Partial unfolding of a protein is not sufficient, by itself, to cause aggregation. They must also follow an assembly reaction, wherein two or more protein molecules aggregate. The kinetics of this process are modulated by protein-protein intermolecular energies, which can in turn be altered by changing solution conditions. Such "colloidal" stability can be related to the second osmotic virial coefficient, B22. This parameter is greatly affected by charge-charge interactions between protein molecules. Hence, changes in solution pH and ionic strength alter protein-protein interactions.

The surface area of proteinaceous material adhered on the surface of a particle of organopolysiloxane can be estimated using a theoretical model of a perfect droplet having a surface area equal to particle volume$^{2/3}$. See J. H. Jett et al., "Quantitation of Cell Surface Antigen Density by Flow Cytometry", 4$^{th}$ Annual Symposium of Flow Cytometry, Voss, Norway (Jun. 4, 1979) (published Jan. 1, 1979) (Abstract). Confirmation of the detection of fluorescently-labeled protein associated on the surface of the fluorescently-labeled organopolysiloxane in the presence of an optical background is inferred by the slope of the correlated measurements, which is near the theoretical of ten to the two thirds ($10^{2/3}$) power for surface area as a function of volume with perfect spheres.

In some non-limiting embodiments, the present invention provides a method for evaluating the aggregation of a proteinaceous material in a suspension comprising an organopolysiloxane, comprising: (a) providing an aqueous suspension (or emulsion) of a fluorescently-labeled organopolysiloxane and a fluorescently-labeled proteinaceous material; (b) measuring relative particle fluorescence intensity of the fluorescently-labeled organopolysiloxane and the fluorescently-labeled proteinaceous material using fluorescence-activated particle sorting; and (c) comparing the relative intensity of the fluorescently-labeled organopolysiloxane to the relative intensity of the fluorescently-labeled proteinaceous material.

As used herein, "proteinaceous material" means a material comprising at least one protein. As used herein, a "protein" is a large organic compound comprising amino acids arranged in a linear chain and joined together by peptide bonds between the carboxyl and amino groups of adjacent amino acid residues, for example fibrous proteins, globular proteins, and protein complexes. Non-limiting examples of suitable proteinaceous materials for use in the present invention include monoclonal antibodies (mAb or moAb), monospecific antibodies that are identical because they are produced by one type of immune cell that are all clones of a single parent cell. Non-limiting examples of suitable monoclonal antibodies include infliximab, basiliximab, abciximab, daclizumab, gemtuzumab, alemtuzumab, rituximab, palivizumab, trastuzumab and etanercept. Other non-limiting examples of suitable proteinaceous materials include Granulocyte Colony Stimulating Factor (e.g., Neupogen™), erythropoietins (e.g., Recormon™ and Eprex™), interferons (e.g., Avonex™ and Rebif™) and rheumatoid arthritis therapies (e.g., Enbrel™, Humira™, and Orencia™). The proteinaceous material is labeled or has attached thereto a fluorescent moiety capable of fluorescing upon exposure to ultraviolet or infrared light, as discussed in detail below.

In some non-limiting embodiments, the proteinaceous material is present in the solution in a concentration of about 20 to about 600 µg/mL, or about 100 to about 300 µg/mL based upon total volume of the aqueous solution.

The organopolysiloxane can be any organopolysiloxane or silicone oil, for example such as can be used to coat surfaces of medical articles such as syringe barrels. In some non-limiting embodiments, the organopolysiloxane has a viscosity ranging from about 100 to about 1,000,000 centistokes (cSt), prior to any curing step, or about 1,000 cSt to about 100,000 cSt, or about 1,000 cSt to about 15,000 cSt, or about 12,500 cSt.

In some non-limiting embodiments, the organopolysiloxane comprises an alkyl-substituted organopolysiloxane, for example as is represented by the following structural Formula (I):

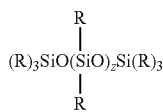
(I)

wherein R is alkyl and Z is about 30 to about 4,500. In some non-limiting embodiments, the organopolysiloxane of Formula (I) can be represented by the following structural Formula (II):

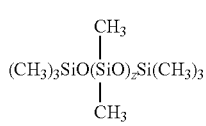
(II)

wherein Z can be as above, or for example can be about 300 to about 2,000, about 300 to about 1,800, or about 300 to about 1,350. In some non-limiting embodiments, the organopolysiloxane is a polydimethylsiloxane, such as DOW CORNING® 360 polydimethylsiloxane or NUSIL polydimethylsiloxane having a viscosity ranging from about 100 to about 1,000,000 cSt.

In some non-limiting embodiments, the organopolysiloxane comprises one or more curable or reactive functional groups, such as alkenyl groups. Each alkenyl group can be independently selected from the group consisting of vinyl, allyl, propenyl, butenyl, pentenyl, hexenyl, heptenyl, octenyl, nonenyl and decenyl. One skilled in the art would understand that the organopolysiloxane can comprise one or more of any of the above types of alkenyl groups and mixtures thereof. In some embodiments, at least one alkenyl group is vinyl. Higher alkenyl or vinyl content provides more efficient crosslinking.

In some non-limiting embodiments, the organopolysiloxane can be represented by the following structural Formulae (III) or (IV):

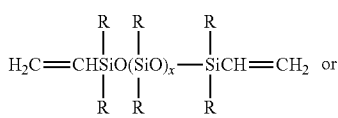
(III)

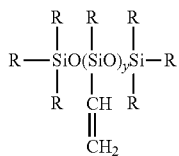
(IV)

wherein R is alkyl, haloalkyl, aryl, haloaryl, cycloalkyl, silacyclopentyl, aralkyl, and mixtures thereof; X is about 60 to about 1,000, preferably about 200 to about 320; and y is about 3 to about 25. Copolymers and mixtures of these polymers also are contemplated.

Non-limiting examples of useful vinyl functional organopolysiloxanes include: vinyldimethylsiloxy terminated polydimethylsiloxanes; trimethylsiloxy terminated vinylmethyl, dimethylpolysiloxane copolymers; vinyldimethylsiloxy terminated vinylmethyl, dimethylpolysiloxane copolymers; divinylmethylsiloxy terminated polydimethylsiloxanes; vinyl, n-butylmethyl terminated polydimethylsiloxanes; and vinylphenylmethylsiloxy terminated polydimethylsiloxanes.

In some embodiments, a mixture of siloxane polymers selected from those of Formulae II, III and/or IV can be used. For example, the mixture can comprise two different molecular weight vinyldimethylsiloxy terminated polydimethylsiloxane polymers, wherein one of the polymers has an average molecular weight of about 1,000 to about 25,000 and preferably about 16,000, and the other polymer has an average molecular weight of about 30,000 to about 71,000 and preferably about 38,000. Generally, the lower molecular weight siloxane can be present in amounts of about 20% to about 80%, such as about 60% by weight of this mixture; and the higher molecular weight siloxane can be present in amounts of about 80% to about 20%, such as about 40% by weight of this mixture.

Another non-limiting example of a suitable vinyl functional organopolysiloxane is (7.0-8.0% vinylmethylsiloxane)-dimethylsiloxane copolymer, trimethylsiloxy terminated, such as VDT-731 vinylmethylsiloxane copolymer which is commercially available from Gelest, Inc. of Morrisville, Pa.

In some non-limiting embodiments, the organopolysiloxane can comprise at least two polar groups. Each polar group can be independently selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, and carboxypropyl groups. One skilled in the art would understand that the organopolysiloxane can comprise one or more of any of the above polar groups and mixtures thereof. In some non-limiting embodiments, the polar groups are acrylate groups, for example, acryloxypropyl groups. In other embodiments, the polar groups are methacrylate groups, such as methacryloxypropyl groups. The organopolysiloxane having polar groups can further comprise one or more alkyl groups and/or aryl groups, such as methyl groups, ethyl groups, or phenyl groups.

Non-limiting examples of such organopolysiloxanes include [15-20% (acryloxypropyl)methylsiloxane]-dimethylsiloxane copolymer, such as UMS-182 acrylate functional siloxane, which is available from Gelest, Inc. of Morrisville, Pa., and SILCOLEASE® PC970 acrylated silicone polymer, which is available from Rhodia-Silicones.

In some non-limiting embodiments, such an organopolysiloxane can be represented by the Formula (V):

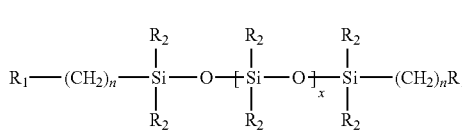
(V)

wherein $R_1$ is selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, carboxypropyl, and fluoro groups; and $R_2$ is alkyl, n ranges from 2 to 4, and x is an integer sufficient to give the lubricant a viscosity of about 100 to 1,000,000 cSt.

In some non-limiting embodiments, the organopolysiloxane can further comprise one or more fluoro groups, such as —F or fluoroalkyl groups such as trifluoromethyl groups. Other useful organopolysiloxanes include polyfluoroalkylmethyl siloxanes and fluoroalkyl, dimethyl siloxane copolymers.

In some non-limiting embodiments, the composition can further comprise one or more cyclic siloxane(s), for example, octamethylcyclotetrasiloxane and/or decamethylcyclopentasiloxane.

In some non-limiting embodiments, the organopolysiloxane can be represented by the following structural Formula (VI):

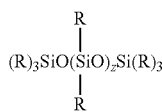

(VI)

wherein R is haloalkyl, aryl (such as phenyl), haloaryl, cycloalkyl, silacyclopentyl, aralkyl and mixtures thereof; and Z is about 20 to about 1,800.

In some non-limiting embodiments, the organopolysiloxane comprises at least two pendant hydrogen groups. Non-limiting examples of suitable organopolysiloxanes comprising at least two pendant hydrogen groups include organopolysiloxanes having pendant hydrogen groups along the polymer backbone or terminal hydrogen groups. In some non-limiting embodiments, the organopolysiloxane can be represented by the following structural Formulae (VII):

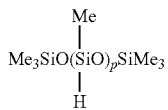

(VII)

wherein p is about 8 to about 125, for example, about 30. In other non-limiting embodiments, the organopolysiloxane can be represented by the following structural Formula (VIII):

$HMe_2SiO(Me_2SiO)_pSiMe_2H$ (VIII)

wherein p is about 140 to about 170, for example, about 150 to about 160. A mixture of these polymers can be used comprising two different molecular weight materials. For example, about 2% to about 5% by weight of the mixture of a trimethylsiloxy terminated polymethylhydrosiloxane having an average molecular weight of about 400 to about 7,500, for example about 1900, can be used in admixture with about 98% to about 95% of a dimethylhydro siloxy-terminated polydimethylsiloxane having an average molecular weight of about 400 to about 37,000 and preferably about 12,000. Non-limiting examples of useful organopolysiloxanes comprising at least two pendant hydrogen groups include dimethylhydro terminated polydimethylsiloxanes; methylhydro, dimethylpolysiloxane copolymers; dimethylhydrosiloxy terminated methyloctyl dimethylpolysiloxane copolymers; and methylhydro, phenylmethyl siloxane copolymers.

In some non-limiting embodiments, the composition comprises hydroxy functional siloxanes, for example a hydroxy functional siloxane comprising at least two hydroxyl groups, such as for example:

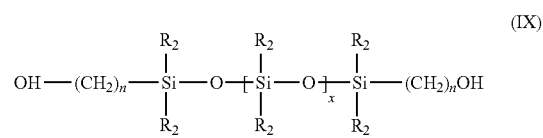

wherein $R_2$ is alkyl, n ranges from 0 to 4, and x is an integer sufficient to give the lubricant a viscosity of about 100 to 1,000,000 cSt. In some non-limiting embodiments, moisture-curable siloxanes which have moisture-curing character as a result of functionality include siloxanes having functional groups such as: alkoxy; aryloxy; oxime; epoxy; —OOCR; N,N-dialkylamino; N,N-dialkylaminoxy; N-alkylamido; —O—NH—C(O)—R; —O—C(=NCH$_3$)—NH—CH$_3$; and —O—C(CH$_3$)=CH$_2$, wherein R is H or hydrocarbyl. As used herein, "moisture-curable" means that the siloxane is curable at ambient conditions in the presence of atmospheric moisture.

Mixtures of any of the organopolysiloxanes discussed above can be used in the present invention.

In some non-limiting embodiments, the organopolysiloxane comprises about 0.001 to about 1 weight percent of the solution.

The proteinaceous material and organopolysiloxane are each labeled with a fluorescent moiety that fluoresces at a different, substantially non-overlapping wavelength of light. Also, if more than one type proteinaceous material and/or more that one type of organopolysiloxane is present, each different type of proteinaceous material and/or each different type of organopolysiloxane can be labeled with a fluorescent moiety that fluoresces at a different, substantially non-overlapping wavelength of light.

As used herein, a "different type" of proteinaceous material means a chemically different proteinaceous material, for example the first proteinaceous material has at least one different atom or different configuration of atoms from the second type of proteinaceous material. Similarly, as used herein, a "different type" of organopolysiloxane means a chemically different organopolysiloxane, for example the first organopolysiloxane has at least one different atom or different configuration of atoms from the second type of organopolysiloxane.

The respective fluorescent moieties used to label the proteinaceous material(s) and organopolysiloxane(s) are selected for excitation and/or emission characteristics to minimize optical background contributions which can result from the spectral emission of one fluorescent moiety appearing in the detector used to measure the other fluorescent moiety.

The organopolysiloxane is labeled with a first fluorescent moiety which emits light within a first range of wavelengths and the proteinaceous material is labeled with a second fluorescent moiety which emits light within a second range of wavelengths when the first fluorescent moiety and the second fluorescent moiety are each exposed to light of the same wavelength emitted by a laser, wherein the first range of wavelengths is substantially free of overlap with the second range of wavelengths.

As used herein, "substantially non-overlapping" means the respective fluorochromes are selected such that their emission spectra have minimal or no significant overlap when excited by the same laser. In some non-limiting embodiments, "substantially non-overlapping" can mean that the first range of wavelengths overlap with the second range of wavelengths less than 5% on a basis of total combined normalized range of wavelengths of the first range of wavelengths and the second range of wavelengths, or less than 2%, or less than 1%. For example, the organopolysiloxane can be labeled with Nile Red fluorescent moiety which emits undetectable levels of light over a range of 450 nm to 650 nm and the proteinaceous material can be labeled with Pacific Blue dye which emits light over a range of 340 nm to 450 nm when exposed to a 405 nm violet laser.

This approach maximizes the detection sensitivity for small amounts of a first fluorescently labeled material by minimizing optical background contributions from other materials labeled with different fluorescent moieties. For example, the detection sensitivity for small amounts of labeled protein can be enhanced by minimizing optical background contributions from fluorescently labeled organopolysiloxane. This can be desirable for detection sensitivity if there is any free labeled protein not associated with an oil droplet remaining in the surrounding buffer.

The labeling of the proteinaceous material(s) and organopolysiloxane(s) will now be discussed with reference to a single type of proteinaceous material and a single type of organopolysiloxane, although one skilled in the art would appreciate that the same concept of using moieties that fluoresce at substantially different wavelengths can be used for multiple proteinaceous material(s) and multiple organopolysiloxane(s). In some non-limiting embodiments, the fluorescent moiety conjugated to the protein can be selected from moieties that excite with a violet (405 nm), blue (488 nm), or red (635 nm) laser as long as the emission band does not substantially overlap that of the other fluorescent moiety or dye selected to label the organopolysiloxane, as discussed above.

Figure 11:
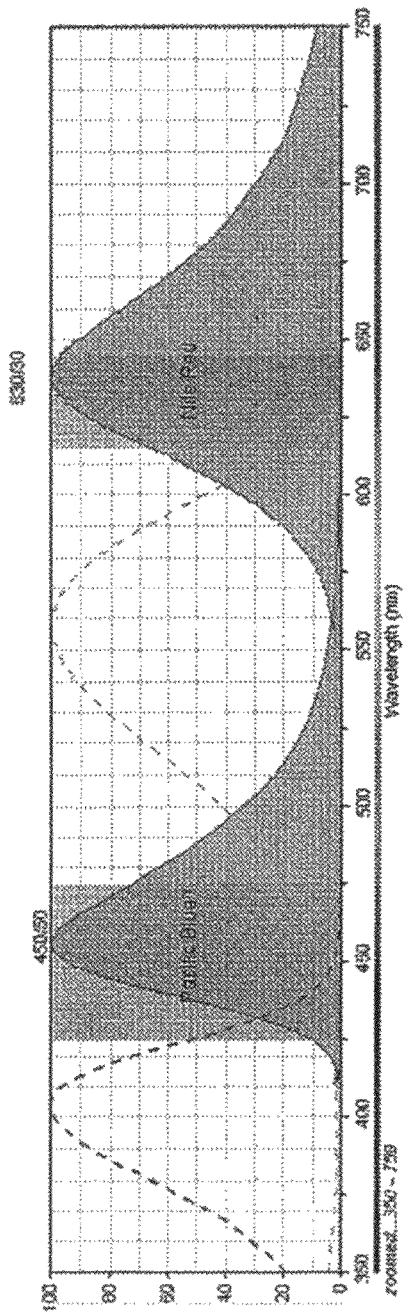
FIG. 11 is a plot of the normalized fluorescence excitation and emission spectra as a function of wavelength for Pacific Blue™ dye and Nile Red dye.

For example, as shown in FIG. 11, Nile Red may be used to label the organopolysiloxane and excites or emits over a broad range (from 450 nm to 650 nm with a maximum near 559 nm), or from 575 nm to 750 nm, and may be used with either a blue or green laser. If using Nile Red to label oil, it is desirable to choose a label for the protein that excites and emits in a different region of the spectrum, and to make the measurements using a flow cytometer system with spatially separated lasers to gain optimal sensitivity. Non-limiting examples of fluorescent moieties suitable for use to label the proteinaceous material when the organopolysiloxane is labeled with Nile Red include Pacific Blue™ dye based on the 6,8-difluoro-7-hydroxycoumarin fluorophore (Invitrogen Corporation, Carlsbad, Calif.) which excites over a specific range from 340 nm to 450 nm with a maximum near 403 nm and may be used with a violet laser; BD Horizon™ V450 (Becton Dickinson) which excites over a specific range (from 340 nm to 450 nm with a maximum near 403 nm) and may be used with a violet laser; Cyan Fluorescent Protein (CFP) which excites over a specific range from 350 nm to 495 nm with a maximum near 435 nm and may be used with a violet laser; AmCyan 108 kDa protein derived from Anemonia Majano (Becton Dickinson) which excites over a specific range (from 360 nm to 500 nm with a maximum near 458 nm and may be used with a violet laser; QDot® 525 (Invitrogen Corporation) which excites over a specific range from <300 nm to 520 nm and may be used with a violet laser; and QDot® 545 (Invitrogen Corporation) which excites over a specific range from <300 nm to 540 nm and may be used with a violet laser. Alternatively, Nile Red can be used to label the proteinaceous material and one of the other dyes discussed immediately above can be used to label the organopolysiloxane.

Alternatively, a variety of lipophilic dyes, such as 1,6-diphenyl-1,3,5-hexatriene (DPH), dioctadecyl-indocarbocyanine (DiL), 3,3'-dioctadecyloxacarbocyanine perchlorate (DiO), DiIC18(5) (DiD), 1,1'-dioctadecyl-3,3,3',3'-tetramethylindotricarbocyanine iodide (DiR), or any other lipophilic dyes can be used to label the organopolysiloxane by a variety of means well known to those skilled in the art to make specific use of various lasers and regions of the fluorescence spectrum that will minimally impact any simultaneous high sensitivity measurements required using other regions of the spectrum to detect fluorescently labeled protein. For example, if DiD is used to label organopolysiloxane (red laser excitation and emission near 670 nm), all of the excitation and emission ranges below that would be usable to detect one or more fluorescently labeled proteins, enabling the use of UV, violet, blue, or green laser excited fluorochromes without substantial overlap in their emission spectrum to be used to label the proteinaceous material.

In some embodiments, the fluorescent moiety can be selected from moieties that fluoresce in the green range (525-585 nm) (usually labeled FL1), such as FITC Fluorescein Isothiocyanate, Alexa Fluor 488, DyLight 488, GFP Green Fluorescence Protein, CFDA-SE Carboxyfluorescein Diacetate Succinimidyl Ester, PI Phosphoinositide; in the orange range (usually FL2), such as PE R-Phycoerythrine; in the red range (usually FL3): PerCP Peridinin Chlorophyll Protein, PE-Cy5 R-Phycoerythrin Cyanine 5, PE-Alexa Fluor 700, PE-Cy5.5 R_Phycoerythrin Cyanine 5.5; in the infra-red range (usually FL4): PE-Alexa Fluor 750, PE-Cy7; using red diode laser (635 nm).

For scanned particles, forward light scatter (FSC, narrow angle light scatter) and side light scatter (SSC, 90° light scatter) fluorescence from violet laser (405 nm), blue laser (488 nm), green laser (532 nm), yellow laser (561 nm), and red laser (635 nm) excited fluorochromes may be used. In some non-limiting embodiments, the proteinaceous material can be chemically labeled with Alexa Fluor® 488 dye (Invitrogen Corporation, Carlsbad, Calif.) according to well-documented protocols (MP 00143, Amine-Reactive Probes, Invitrogen Corporation). In other non-limiting embodiments, the proteinaceous material can be chemically labeled with Pacific Blue™ dye according to methods well known to those skilled in the art, such as by using suitable commercial kits available from Invitrogen. To label the organopolysiloxane, Nile Red dye can be dissolved in organopolysiloxane at 5 mg/mL. Nile Red, 9-diethylamino-5-benzophenoxazine-5-one, is an extremely hydrophobic dye whose fluorescence is fully quenched in water.

Pacific Blue™ dye has an excitation maximum at 404 nm and an emission maximum of 455 nm, and Nile Red dye has an excitation maximum at 559 nm emission maximum of 637 nm. Nile Red essentially does not excite at the violet laser wavelength which minimizes the optical background from the organopolysiloxane in the detector used to measure the protein particles. Conversely, when the particles traverse the blue laser, Pacific Blue™ dye does not excite minimizing signal spillover into the Nile Red detector. Suspensions with chemically labeled mAb and dyed organopolysiloxane can be scanned with BD FACScan™ Flow Cytometer analyzer or a multilaser BD FACSCanto™ Flow Cytometer analyzer or BD™ LSR II Flow Cytometer (Becton, Dickinson and Company, Franklin Lakes, N.J.).

Flow cytometry is an analytical process for counting, examining, and sorting microscopic particles suspended in a stream of fluid. It allows simultaneous multiparametric analysis of the physical and/or chemical characteristics of single particles flowing through an optical and/or electronic detection apparatus. In the flow cytometer, one or more beams of monochromatic light (usually laser light) are focused onto a hydrodynamically focused stream of fluid containing the sample. A plurality of detectors are aligned to the point where the stream passes through the light beam; one in line with the primary light beam (Forward Scatter or FSC) and several perpendicular to it (Side Scatter or SSC) and one or more fluorescent detectors. Each suspended particle passing through the tightly focused beam scatters the light in a variety of directions according to Mie theory, and fluorescent labels attached to the particle may be excited into emitting light at a lower frequency than the light source. This combination of scattered and fluorescent light is detected by the detectors. By analyzing fluctuations in brightness at each detector (one for each fluorescent emission peak) it is possible to derive various types of information about the physical and chemical structure of each individual particle. FSC generally correlates well with the particle size and refractive characteristics and SSC depends upon the size and inner complexity of the particle (i.e., shape of a cell nucleus, the amount and type of particle or the particle roughness). Some flow cytometers form images of each particle's fluorescence, scattered light, and transmitted light.

Flow cytometers are capable of analyzing several thousand particles every second, and multilaser FACS cell sorters such as the BD FACSAria™ II and BD™ Influx sorting platforms can actively separate and isolate particles having specified properties. A flow cytometer includes a flow cell-liquid stream (solution) which carries and aligns the cells so that they pass single file through the light beam for sensing; one or more light sources, such as a mercury or xenon lamp, high power water-cooled lasers (argon, krypton, dye laser), low power air-cooled lasers (argon (488 nm), red-HeNe (633 nm), green-HeNe, HeCd (UV)), or diode lasers (blue, green, red, violet); multiple detectors which generate FSC and SSC as well as fluorescence signals, an Analog to Digital Conversion (ADC) system, a linear or logarithmic amplification system, and a computer for analysis of the signals. The data generated by flow-cytometers can be plotted as a single parameter histogram, as two dimensional dot plots (scatter grams, density or contour plots) or even as three dimensional isometric displays. Graphical regions of interest may be drawn to define populations of interest, and are usually combined by implied Boolean AND logic in the form of a hierarchal gate tree, in which the term gate refers to one or more combined regions of interest within which the particles of interest reside. The plots are often made on logarithmic scales whenever the data has a large dynamic range, up to 4 or 5 decades. Because different fluorescent dyes' emission spectra overlap, signals from the detectors may be compensated electronically as well as computationally. However, while this process realigns the population medians, the effects from photon statistics from the original measurement remain, resulting in "spread" among significantly realigned populations (i.e, where the background contributions from other fluorescent signals were significant). Typically, data acquired using the flow cytometer are re-analyzed post acquisition with software such as BD FACSDiva Software.

Fluorescence-activated cell sorting or particle sorting is a specialized type of flow cytometry. It provides a method for sorting a heterogeneous mixture of particles into two or more containers, one cell at a time, based upon the specific light scattering and fluorescent characteristics of each cell. It records fluorescent signals from individual cells, and physically separates cells of particular interest. The acronym FACS is trademarked and owned by Becton Dickinson.

The particle suspension is entrained in the center of a narrow, rapidly flowing stream of liquid. The flow is arranged so that on the average (Poisson distribution) there is a large separation between particles relative to their diameter. A vibrating mechanism causes the stream of particles to break into individual droplets. The system is adjusted so that there is a low probability of more than one particle being in a droplet. Just before the stream breaks into droplets the flow passes through one or more laser intersects where the fluorescent character of interest of each particles are measured. If a particle is to be collected, a charge is applied to the flow cell during the period of time one or more drops form and break off from the stream. These charged droplets then fall through an electrostatic deflection system that diverts droplets into target containers based upon the charge applied to the droplet.

By using an apparatus such as a fluorescence activated particle scanning device or FACS™ flow cytometer, relative particle fluorescence intensity of the fluorescently-labeled organopolysiloxane and the fluorescently-labeled proteinaceous material can be determined using fluorescence-activated particle sorting. The relative intensity of the fluorescently-labeled organopolysiloxane can be compared to the relative intensity of the fluorescently-labeled proteinaceous material and the amount of proteinaceous material aggregated or agglomerated with the organopolysiloxane can be determined. "Aggregation" of the proteinaceous material with the organopolysiloxane includes proteinaceous material adsorption to organopolysiloxane as well as proteinaceous material aggregation nucleated by organopolysiloxane, and includes any irreversible association between organopolysiloxane and the proteinaceous material.

Each solution can be analyzed by fluorescence activated particle scanning to determine particle composition. Fluorescence activated particle scanning can be used to analyze particle size, morphology, and relative particle fluorescence. Other useful analyses include determination of suspension turbidity, silicone oil droplet number concentration, and silicone oil droplet size distribution. Optical densities can be determined using a PerkinElmer Lambda 35 spectrophotometer (Wellesley, Mass.). After brief and gentle agitation to deflocculate droplet agglomerates, silicone oil suspension optical densities can be measured at 660 nm as functions of time and formulation condition. In aqueous filtrate, proteinaceous material absorbance at 280 nm can be measured to determine mAb concentrations. Alternatively, proteinaceous material concentrations can be measured with a Coomassie dye binding assay (Coomassie Plus™ Better Bradford Assay Kit, Pierce Biotechnology, Rockford, Ill.).

Silicone oil droplet size distributions can be measured using a Coulter LS230 laser diffraction particle size analyzer (Beckman Coulter, Fullerton, Calif.). Relative size distributions can be measured for suspensions immediately after homogenization and as a function of time up to 2 weeks after suspension preparation. From silicone oil droplet relative size distributions and number concentrations, total silicone oil surface area can be estimated.

In some non-limiting embodiments, the relative particle fluorescence intensity of the fluorescently-labeled organopolysiloxane and the fluorescently-labeled proteinaceous material can be determined using FRET (fluorescence resonance energy transfer or Förster resonance energy transfer) in which the donor fluorescence moiety is attached to the oil and the acceptor fluorescence moiety is attached to the protein. By using FRET technology, the emission from the acceptor would not occur unless it were in extremely close contact with the oil surface, which may enable more precise measurement. A donor chromophore in its excited state can transfer energy by a non-radiative, long-range dipole-dipole coupling mechanism to an acceptor chromophore in close proximity (typically <10 nm). For monitoring the complex formation between two molecules, one of them is labeled with a donor and the other with an acceptor, and these fluorophore-labeled molecules are mixed. When the molecules dissociated, the donor emission is detected upon the donor excitation. On the other hand, when the donor and acceptor are in proximity (1-10 nm) due to the interaction of the two molecules, the acceptor emission is predominantly observed because of the intermolecular FRET from the donor to the acceptor.

In some non-limiting embodiments, the aqueous suspension further comprises at least one non-ionic surfactant. The non-ionic surfactant can reduce silicone oil coalescence rates. Thus, suspended oil droplets remain in solution longer when non-ionic surfactant is present.

Non-limiting examples of suitable non-ionic surfactants include acetylenic glycols, alkanolamides, alkanolamines, alkyl phenols, fatty acids, fatty alcohols, fatty esters, glycerol esters, monododecyl ethers, phenol derivatives, poloxamers, poloxamines, polyoxyethylene acyl ethers, polyoxyethyleneglycol dodecyl ethers, sorbitols, sorbitan derivatives and mixtures thereof. In some non-limiting embodiments, the non-ionic surfactant is a sorbitan derivative selected from the group consisting of sorbitan fatty acid esters, polyoxyethylene sorbitan fatty acid esters and mixtures thereof. In some non-limiting embodiments, the non-ionic surfactant is a polyoxyethylene sorbitan fatty acid ester, such as Tween 20® polyoxyethylene 20 sorbitan monolaurate, also known as Polysorbate 20. Other useful polyoxyethylene sorbitan fatty acid esters include Polysorbate 21, Polysorbate 40, Polysorbate 60, Polysorbate 61, Polysorbate 65, Polysorbate 80, Polysorbate 81, Polysorbate 85 or Polysorbate 120.

The amount of non-ionic surfactant in the solution can range from about 0.001 to about 0.5 weight percent on a basis of total weight of the aqueous solution.

In some non-limiting embodiments, the aqueous suspension further comprises at least one sugar. Sugar can enhance the rate of organopolysiloxane coalescence, such that less surface area of organopolysiloxane is available to attract proteinaceous material. Suitable sugars include monosaccharides, disaccharides, trisaccharides, oligosaccharides and mixtures thereof. Non-limiting examples of suitable sugars include sucrose, lactose, fructose, glucose, galactose, mannose, trehalose and mixtures thereof.

The amount of sugar in the solution can range from about 0.005 to about 10 weight percent on a basis of total weight of the aqueous solution.

The combined presence of sugar and non-ionic surfactant can further reduce aggregation of proteinaceous material. In some non-limiting embodiments, the solution can comprise at least one sugar and at least one non-ionic surfactant, such as polyoxyethylene sorbitan fatty acid ester and sucrose, in amounts or concentrations such as are describe above.

In some non-limiting embodiments, the method further comprises providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein a concentration of the at least one aggregation inhibitor is different in each aqueous suspension, measuring relative particle fluorescence intensity of the fluorescently-labeled organopolysiloxane and the fluorescently-labeled proteinaceous material in each aqueous suspension using fluorescence-activated particle sorting; and comparing the relative intensity of the fluorescently-labeled organopolysiloxane to the relative intensity of the fluorescently-labeled proteinaceous material for each aqueous suspension.

In some non-limiting embodiments, the method further comprises providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein the at least one aggregation inhibitor is different in each aqueous suspension, measuring relative particle fluorescence intensity of the fluorescently-labeled organopolysiloxane and the fluorescently-labeled proteinaceous material in each aqueous suspension using fluorescence-activated particle sorting; and comparing the relative intensity of the fluorescently-labeled organopolysiloxane to the relative intensity of the fluorescently-labeled proteinaceous material for each aqueous suspension. The aggregation inhibitor in each solution is chemically different or of a different type, for example different sugars and/or different non-ionic surfactants.

Figure 10:
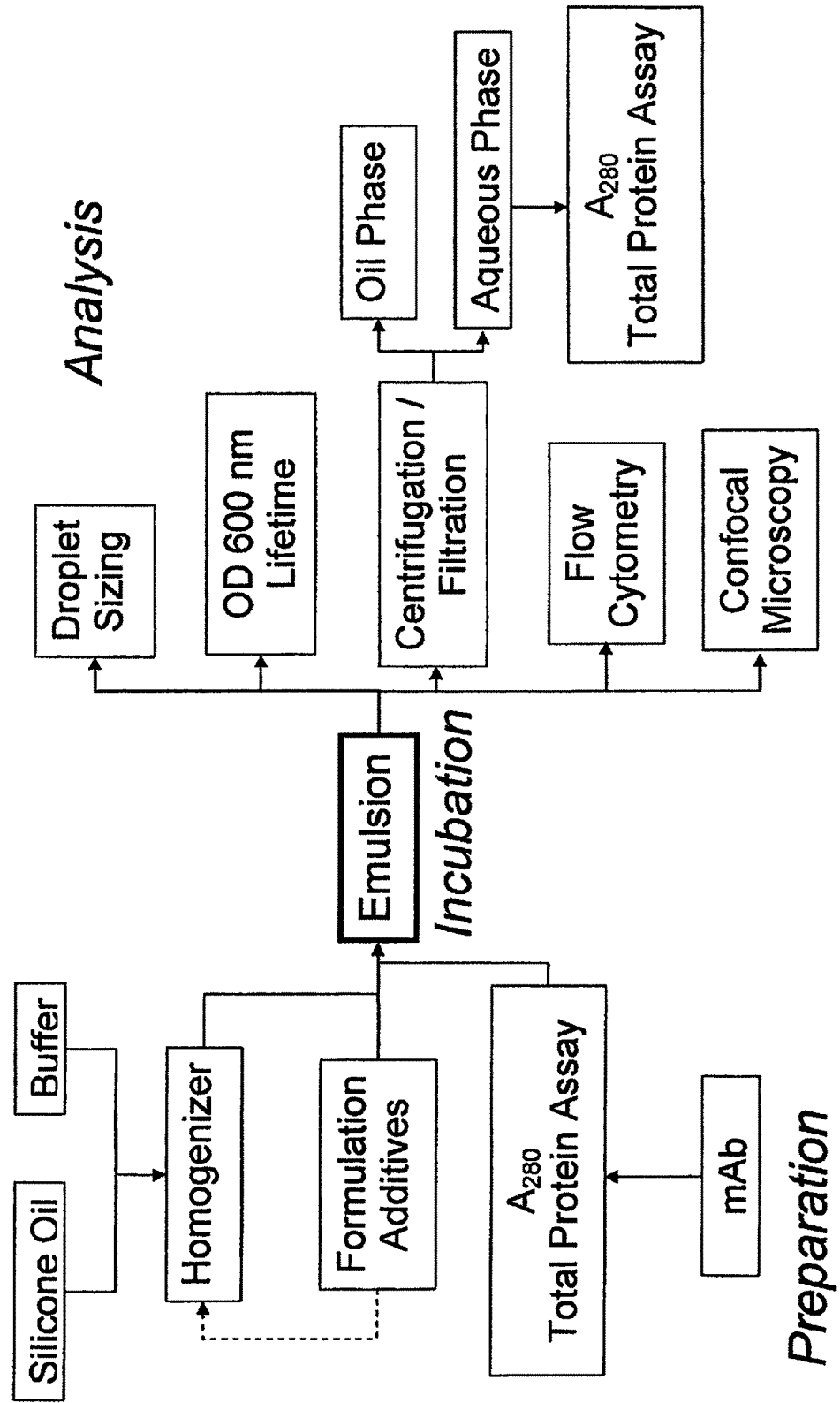
FIG. 10 is a flow chart of a method for preparing and analyzing samples of organopolysiloxane solutions according to the present invention.

Referring to FIG. 10, there is shown a flow chart for a method for preparing and analyzing samples of organopolysiloxane solutions according to the present invention. The solutions can be prepared and analyzed as discussed above and in detail in Example A below.

In some non-limiting embodiments, the method further comprises selecting at least one aggregation inhibitor for use in a suspension comprising a proteinaceous material based upon the comparison of the relative intensity of the fluorescently-labeled organopolysiloxane to the relative intensity of the fluorescently-labeled proteinaceous material for each aqueous suspension.

In some non-limiting embodiments, the present invention provides a method for inhibiting the aggregation of a proteinaceous material in a suspension comprising an organopolysiloxane, comprising: (a) providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein (i) the at least one aggregation inhibitor is different in each aqueous suspension, or (ii) the amount of aggregation inhibitor is different in each aqueous solution; (b) measuring relative particle fluorescence intensity of the fluorescently-labeled organopolysiloxane and the fluorescently-labeled proteinaceous material in each aqueous suspension using fluorescence-activated particle sorting; (c) comparing the relative intensity of the fluorescently-labeled organopolysiloxane to the relative intensity of the fluorescently-labeled proteinaceous material for each aqueous suspension; and (d) selecting at least one aggregation inhibitor for use in a suspension comprising a proteinaceous material based upon the comparison of the relative intensity of the fluorescently-labeled organopolysiloxane to the relative intensity of the fluorescently-labeled proteinaceous material for each aqueous suspension.

By one or more of the above methods, a suitable combination of sugar and non-ionic surfactant (and suitable concentrations thereof) can be determined for use in medical articles which use an organopolysiloxane coating on surfaces in contact with a solution comprising proteinaceous material.

In some non-limiting embodiments, the present invention provides a medical article, comprising: (a) a container comprising a chamber for receiving a solution, wherein the inner surface of the chamber has a coating thereon prepared from a composition comprising an organopolysiloxane; and (b) a solution comprising: (i) at least one proteinaceous material; (ii) at least one non-ionic surfactant; and (iii) at least one sugar.

As used herein, "medical article" means an article or device that can be useful for medical treatment. Non-limiting examples of medical articles include syringe assemblies, drug cartridges, needleless injectors, liquid dispensing devices and liquid metering devices. In some embodiments, the medical article is a syringe assembly comprising a syringe chamber or barrel (for receiving the solution comprising proteinaceous material, for example) and a sealing member.

The chamber can be formed from glass, metal, ceramic, plastic, rubber, or combinations thereof. In some non-limiting embodiments, the chamber is prepared from one or more olefinic polymers, such as polyethylene, polypropylene, poly (1-butene), poly(2-methyl-1-pentene), and/or cyclic polyolefin. For example, the polyolefin can be a homopolymer or a copolymer of an aliphatic monoolefin, the aliphatic monoolefin preferably having about 2 to 6 carbon atoms, such as polypropylene. In some non-limiting embodiments, the polyolefin can be basically linear, but optionally may contain side chains such as are found, for instance, in conventional, low density polyethylene. In some non-limiting embodiments, the polyolefin is at least 50% isotactic. In other embodiments, the polyolefin is at least about 90% isotactic in structure. In some non-limiting embodiments, syndiotactic polymers can be used. In some embodiments, cyclic polyolefins can be used. Non-limiting examples of suitable cyclic polyolefins include norbornene polymers such as are disclosed in U.S. Pat. Nos. 6,525,144, 6,511,756, 5,599,882, and 5,034,482 (each of Nippon Zeon), 7,037,993, 6,995,226, 6,908,970, 6,653,424 and 6,486,264 (each of Zeon Corp.), 7,026,401 and 6,951,898 (Ticona), 6,063,886 (Mitsui Chemicals), 5,866,662, 5,856,414, 5,623,039 and 5,610,253 (Hoechst), 5,854,349 and 5,650,471 (Mitsui Petrochemical and Hoechst) and as described in "Polycyclic olefins", process Economics Program (July 1998) SRI Consulting, each of the foregoing references being incorporated by reference herein. Non-limiting examples of suitable cyclic polyolefins include Apel™ cyclic polyolefins available from Mitsui Petrochemical, Topas™ cyclic polyolefins available from Ticona Engineering Polymers, Zeonor™ or Zeonex™ cyclic polyolefins available from Zeon Corporation, and cyclic polyolefins available from Promerus LLC.

The polyolefin can contain a small amount, generally from about 0.1 to 10 percent, of an additional polymer incorporated into the composition by copolymerization with the appropriate monomer. Such copolymers may be added to the composition to enhance other characteristics of the final composition, and may be, for example, polyacrylate, polystyrene, and the like.

In some non-limiting embodiments, the chamber may be constructed of a polyolefin composition which includes a radiation stabilizing additive to impart radiation stability to the container, such as a mobilizing additive which contributes to the radiation stability of the container, such as for example those disclosed in U.S. Pat. Nos. 4,959,402 and 4,994,552, assigned to Becton, Dickinson and Company and both of which are incorporated herein by reference.

The other component of the medical article in contact with the chamber is the sealing member. The sealing member can be formed from any elastomeric or plastic material. Elastomers are used in many important and critical applications in medical devices and pharmaceutical packaging. As a class of materials, their unique characteristics, such as flexibility, resilience, extendability, and sealability, have proven particularly well suited for products such as catheters, syringe tips, drug vial articles, tubing, gloves, and hoses. Three primary synthetic thermoset elastomers typically are used in medical applications: polyisoprene rubber, silicone rubber, and butyl rubber. Of the three rubbers, butyl rubber has been the most common choice for articles due to its high cleanness and permeation resistance which enables the rubber to protect oxygen- and water-sensitive drugs.

Suitable butyl rubbers useful in the method of the present invention include copolymers of isobutylene (about 97-98%) and isoprene (about 2-3%). The butyl rubber can be halogenated with chlorine or bromine. Suitable butyl rubber vulcanizates can provide good abrasion resistance, excellent impermeability to gases, a high dielectric constant, excellent resistance to aging and sunlight, and superior shock-absorbing and vibration-damping qualities to articles formed therefrom. Non-limiting examples of suitable rubber stoppers include those available from West Pharmaceuticals, American Gasket Rubber, Stelmi, and Helvoet Rubber & Plastic Technologies BV.

Other useful elastomeric copolymers include, without limitation, thermoplastic elastomers, thermoplastic vulcanizates, styrene copolymers such as styrene-butadiene (SBR or SBS) copolymers, styrene-isoprene (SIS) block polymers or styrene-isoprene/butadiene (SIBS), in which the content of styrene in the styrene block copolymer ranges from about 10% to about 70%, and preferably from about 20% to about 50%. Non-limiting examples of suitable styrene-butadiene stoppers are available from Firestone Polymers, Dow, Reichhold, Kokoku Rubber Inc., and Chemix Ltd. Other suitable thermoplastic elastomers are available from GLS, Tecknor Apex, AES, Mitsubishi and Solvay Engineered Polymers, for example. The elastomer composition can include, without limitation, antioxidants and/or inorganic reinforcing agents to preserve the stability of the elastomer composition.

In some embodiments, the sealing member can be a stopper, O-ring, plunger tip, or piston, for example. Syringe plunger tips or pistons typically are made of a compressible, resilient material such as rubber, because of the rubber's ability to provide a seal between the plunger and interior housing of the syringe. Syringe plungers, like other equipment used in the care and treatment of patients, have to meet high performance standards, such as the ability to provide a tight seal between the plunger and the barrel of the syringe.

The organopolysiloxane coating is applied to at least a portion of the sliding surface(s) of the chamber and/or sealing member. In some embodiments, the chamber is coated with the coating described below and the sealing member is uncoated or coated with a polydimethylsiloxane coating. In other embodiments, the sealing member is coated with the coating described below and the chamber is uncoated or coated with a polydimethylsiloxane coating. In other embodiments, both the chamber and sealing member are coated with coatings as described below.

The chamber and/or sealing member is coated with a coating prepared from a composition comprising one or more organopolysiloxane(s). Application of a coating to the inner surface of the chamber or outer surface of the sealing member may be accomplished by any suitable method, as, for example, dipping, brushing, spraying, and the like. The composition may be applied neat or it may be applied in a solvent, such as low molecular weight silicone, non-toxic chlorinated or fluorinated hydrocarbons, for example, 1,1,2-trichloro-1,2,2-trifluoroethane, freon or conventional hydrocarbon solvents such as alkanes, toluene, petroleum ether, and the like where toxicology is not considered important. The solvent is subsequently removed by evaporation. The coating may be of any convenient thickness and, in practice, the thickness will be determined by such factors as the quantity applied, viscosity of the lubricant, and the temperature of application. For reasons of economy, the coating preferably is applied as thinly as practical, since no significant advantage is gained by thicker coatings. The exact thickness of the coating does not appear to be critical and very thin coatings, i.e., one or two microns exhibit effective lubricating properties. While not necessary for operability, it is desirable that the thickness of the coating be substantially uniform throughout. The coating can be partially or fully crosslinked after application or partially crosslinked to attach to the substrate, and then fully crosslinked at a later time.

The coated chamber and/or coated sealing member can be subjected to oxidative treatment, for example, plasma treatment. The plasma treatment may be carried out in any common vacuum or atmospheric plasma generation equipment. Any suitable ionizing plasma may be used, as, for example, a plasma generated by a glow discharge or a corona discharge. The plasma may be generated from a variety of gases or mixtures thereof. Gases frequently used include air, hydrogen, helium, ammonia, nitrogen, oxygen, neon, argon, krypton, and xenon. Any gas pressure may be used, for example, atmospheric pressure or 5 mm of Hg or below, such as about 0.1 to about 1.0 mm of Hg. In some embodiments such as atmospheric oxidative methods, the ionizing plasma is introduced directly from a small port in the chamber or through the opening later sealed by the sealing member. The external surface of the coated sealing member can be treated directly similarly to current corona or plasma treatment methods. In other embodiments, such as vacuum based equipment, the plasma can be excited around the coated sealing member or coated chamber and allowed to diffuse into the chamber and sealing member features. Alternatively, the plasma may be excited within the interior of the open chamber by properly controlling electrode position. After oxidative treatment, the treated chamber and/or treated sealing member can be subjected to heat treatment or irradiation with an isotope (such as gamma radiation), electron beam, or ultraviolet radiation. Alternatively, the treated chamber and/or treated sealing member can be heat treated via oven or radio frequency (RF). In the case of oven crosslinking, temperatures can range from about 120° to about 140° C. and residence time in the oven is generally about 30 to about 40 seconds, depending on the precise formulation. If RF techniques are used, the coil should conduct enough heat to obtain a substrate surface temperature of about 150° to about 200° C. At these temperatures, only about 2 to about 4 seconds are required for cure.

In some embodiments, the coating is at least partially crosslinked by irradiation with an isotope, electron beam, or ultraviolet radiation. This technique has the advantage of sterilizing as well, which is useful in medical applications. Radiation sterilization in the form of ionizing radiation commonly is used in hospitals for medical devices such as catheters, surgical items, and critical care tools. Gamma irradiation exerts a microbicidal effect by oxidizing biological tissue, and thus provides a simple, rapid and efficacious method of sterilization. Gamma rays are used either from a cobalt-60 ($^{60}$Co) isotope source or from a machine-generated accelerated electron source. Sufficient exposures are achieved when the materials to be sterilized are moved around an exposed $^{60}$Co source for a defined period of time. The most commonly used dose for sterilizing medical articles is about 5 to about 100 kGy, for example, 5-50 kGy.

In some embodiments, a surface lubricant layer about 0.3 to 10, preferably about 0.8 to 4.0 microns thick may be applied over the crosslinked organopolysiloxane coating described above. The surface lubricant can be conventional silicone oil (organopolysiloxane) of viscosity about 100 to 1,000,000; 100 to 60,000; or preferably about 1,000 to 12,500 cSt. The surface lubricating layer may be applied by any of the conventional methods described above. The preferred methods for applying the surface lubricant are by spraying or dipping the syringe barrel into a solution, about 4% by weight, of the surface lubricant in a solvent such as chloroform, dichloromethane or preferably a chlorofluorocarbon, such as FREON™ TR The surface lubricant may optionally be lightly crosslinked by oxidative treatment and/or radiation.

In some embodiments in which both the chamber and sealing member are coated with organopolysiloxanes, the viscosity of the organopolysiloxane coating the chamber can be greater than the viscosity of the organopolysiloxane coating the sealing member. For example, the viscosity of the organopolysiloxane coating the chamber can be 12,500 cSt, while the viscosity of the organopolysiloxane coating the sealing member can be 1,000 cSt. In other embodiments, the viscosity of the organopolysiloxane coating the chamber can be equal to or less than the viscosity of the organopolysiloxane coating the sealing member. For example, the viscosity of the organopolysiloxane coating the chamber can be 12,500 cSt, while the viscosity of the organopolysiloxane coating the sealing member can be 100,000 cSt.

In some embodiments, the coated articles are subjected to a sterilization treatment. Many sterilization techniques are available today to sterilize medical devices to eliminate living organisms such as bacteria, yeasts, mold and viruses. Commonly used sterilization techniques used for medical devices include autoclaving, ethylene oxide (EtO) or gamma irradiation, as well as more recently introduced systems that involve low-temperature gas plasma and vapor phase sterilants.

The chamber of the medical article is at least partially filled with the solution comprising: (i) at least one proteinaceous material; (ii) at least one non-ionic surfactant; and (iii) at least one sugar. The components and amounts of the solution are described in detail above. Generally, the solution can be filtered prior to filling the chamber, for example by filtration through a 0.22 μm filter and distributed into the sterile chamber under aseptic conditions well known to those skilled in the art.

The present invention is more particularly described in the following examples, which are intended to be illustrative only, as numerous modifications and variations therein will be apparent to those skilled in the art.

EXAMPLES

Example A

This example studies the effects of sucrose and a non-ionic surfactant (Tween 20® polyoxyethylene 20 sorbitan monolaurate non-ionic surfactant) on aggregation of Herceptin® traztuzumab monoclonal antibody (mAb) and on silicone oil droplet characteristics. In this investigation, no attempt was made to distinguish mAb adsorption to silicone oil from mAb aggregation nucleated by silicone oil. Instead, any irreversible association between silicone oil and mAb is simply referred to as "aggregation".

Four formulations were analyzed in this study, as detailed in Table 1. Each formulation was analyzed by fluorescence activated particle scanning to determine particle composition. For a subset of these formulations, fuller analysis was performed. Suspension turbidity, silicone oil droplet number concentration, and silicone oil droplet size distribution were measured. After filtration, Herceptin® trastuzumab concentrations were measured in aqueous filtrate.

A solution of the recombinant humanized monoclonal antibody (rhmAb) Herceptin® (trastuzumab, Genentech, Inc.) was exchanged into 10 mM sodium acetate, pH 5.0, by extensive dialysis (Pierce Slide-A-Lyzer, 3500 MWCO). Appropriate volumes of separate solutions of sucrose and/or polysorbate 20 (Tween 20) were mixed with purified Herceptin® solutions to a final mAb concentration of 1 mg/mL Concentrations of formulation additives (sucrose, NaCl and surfactants) were systematically varied as described in appropriate results sections. All chemicals were of reagent grade or higher.

TABLE 1

| | Formulation Component | | | |
|---|---|---|---|---|
| Formulation No. | Silicone oil (1% v/v) | mAb (1 mg/mL) | Sucrose (0.5M) | Tween 20 ® Non-ionic surfactant (0.005%) |
| A | x | x | | |
| B | x | x | x | |
| C | x | x | | x |
| D | x | x | x | x |

Suspensions of medical grade silicone oil (ca. 0.5% v/v) in aqueous buffer (10 mM sodium acetate, pH 5.0) were created by high pressure homogenization. Polydimethylsiloxane medical fluid (Dow Corning 360, 1000 cSt) was added to an aqueous buffer and passed once through a high pressure homogenizer (Emulsiflex C5 Homogenizer commercially available from Avestin, Inc.). Final suspensions for analysis were created by mixing mAb solutions containing formulation additives with suspensions of silicone oil in buffer immediately following homogenization.

After varying periods of incubation, suspensions were filtered (Whatman Anotop 10, 0.02 μm syringe filter) to separate aqueous and oil phases. Just prior to filtration, suspensions were held for ca. 2 min. to allow oil droplets near the filter membrane to sediment. As a control to test the degree of phase separation, aqueous nitrate fluorescence was measured after labeling silicone oil with Nile Red dye. Insignificant fluorescence measurements at 628 nm demonstrated adequate separation.

Optical densities of two sample types were measured with a PerkinElmer Lambda 35 spectrophotometer (Wellesley, Mass.). After brief and gentle agitation to deflocculate droplet agglomerates, homogeneous silicone oil suspension optical densities were measured at 660 nm as functions of time and formulation condition. In aqueous filtrate, mAb absorbance at 280 nm was measured to determine mAb concentrations. Alternatively, mAb concentrations were measured with a Coomassie dye binding assay (Coomassie Plus™ Better Bradford Assay Kit, Pierce Biotechnology, Rockford, Ill.).

Silicone oil droplet size distributions were measured using a Coulter LS230 laser diffraction particle size analyzer (Beckman Coulter, Fullerton, Calif.). Relative size distributions were measured for suspensions immediately after homogenization and as a function of time up to 2 weeks after suspension preparation. From silicone oil droplet relative size distributions and number concentrations, total silicone oil surface area was estimated.

Fluorescence activated particle scanning can be used to analyze particle size, morphology, and relative particle fluorescence. Only particles of a threshold size (>1 μm diameter) are analyzed by the technique. For scanned particles, forward light scattering (FSC, 1800 light scattering), side light scattering (SSC, 90° light scattering), green fluorescence intensity (FL1, 525-585 nm) and red fluorescence intensity (FL2, 585-600 nm) were measured. Herceptin® trastuzumab molecules were chemically labeled with Alexa Fluor® 488 dye (Invitrogen Corporation, Carlsbad, Calif.) according to well-documented protocols (MP 00143, Amine-Reactive Probes, Invitrogen Corporation). To label the silicone oil, Nile Red dye was dissolved in silicone oil at 5 mg/mL. Nile Red, 9-diethylamino-5-benzophenoxazine-5-one, is an extremely hydrophobic dye whose fluorescence is fully quenched in water. Alexa Fluor® 488 dye has an emission maximum of 519 nm, and Nile Red dye has an emission maximum of 628 nm. Suspensions with chemically labeled mAb and dyed silicone oil were scanned with a BD FACScan™ Flow Cytometer analyzer (Becton, Dickinson and Company, Franklin Lakes, N.J.).

Figure 1B:
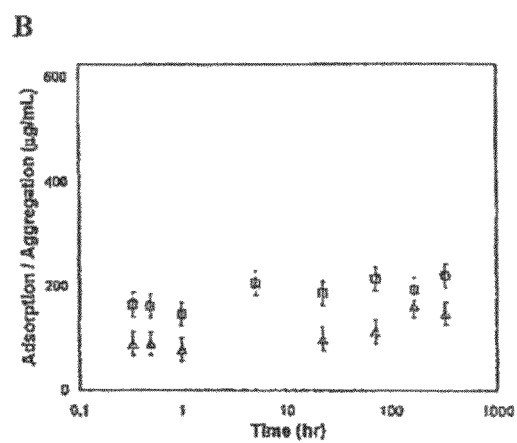
FIG. 1B is a plot of adsorption/aggregation of mAb with silicone oil as a function of time for a formulation including sucrose, mAb and silicone oil and a formulation including sucrose, non-ionic surfactant, mAb and silicone oil according to the present invention.

The degree to which Herceptin® trastuzumab interacts with silicone oil droplets in suspension depends on the formulation environment and incubation time. FIGS. 1A and 1B illustrate the association of mAb with silicone oil. Symbols are arithmetic means of three replicates measured by difference between initial mAb concentration and mAb concentration in filtrate. Error bars represent ±1 standard deviation. In all series, mAb concentration is 1 mg/mL. In both panels, squares denote formulations with 0.5 M sucrose, mAb, and silicone oil. In FIG. 1A, triangles denote formulations with only mAb and oil. In FIG. 1B, triangles denote formulations with 0.5 M sucrose, 0.005% Tween 20® non-ionic surfactant, mAb, and oil.

After suspension, incubation and filtration, formulations with sucrose contained higher concentrations of mAb in aqueous filtrate than those without sucrose at sufficiently long incubation times. Thus, the presence of sucrose reduces mAb aggregation at long times, as shown in FIG. 1A. FIG. 1B compares the formulation with sucrose shown in panel A with a formulation containing sucrose and non-ionic surfactant. The addition of non-ionic surfactant further reduced mAb association with silicone oil.

By measuring fluorescence intensities of particles containing labeled mAb and labeled silicone oil, the effects of formulation additives on mAb aggregation can be better understood. FIGS. 2A-2D illustrate the fluorescence intensity scatter plots of two wavelength bands In FIGS. 2A-2D, FL1 intensity is directly proportional to Alexafluor 488 labeled mAb concentration. FL2 fluorescence intensity is directly proportional to Nile Red labeled silicone oil volume. FL1 and FL2 intensities scale roughly with particle size, encompassing a size range greater than one order of magnitude. Experimental settings were optimized such that the relative intensities of mAb and silicone oil would be equivalent in FIG. 2A. These settings were retained for all other formulations (FIGS. 2B-2D). Thus, trends within and comparisons between panels are meaningful; absolute intensity values are not. Axes units were arbitrary. Histograms represent particle intensity distributions. Histogram scales range from 0 to 0.5. FIGS. 2A-2D depict formulations of 1 mg/mL mAb and silicone oil with various combinations of sucrose and surfactants: A neither sucrose nor surfactant; B 0.5 M sucrose; C 0.005% Tween 20® non-ionic surfactant; and D 0.5 M sucrose and 0.005% Tween 20® non-ionic surfactant.

Each of FIGS. 2A-2D corresponds to the formulation with the same letter in Table 1. Thus, the two panels on the left (FIGS. 2A and 2C) represent formulations without sucrose. The two panels on the right (FIGS. 2B and 2D) represent formulations containing sucrose. From top to bottom, panels represent no surfactant (FIGS. 2A and 2B) and non-ionic surfactant (FIGS. 2C and 2D).

Figure 2A:
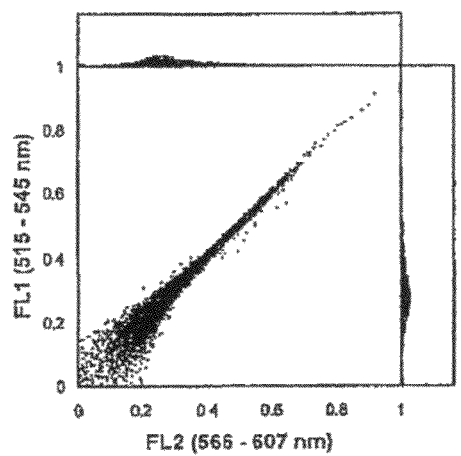
FIG. 2A is a fluorescence intensity scatter plot of FL1 intensity and FL2 intensity for a control formulation without sucrose or surfactant.
Figure 2B:
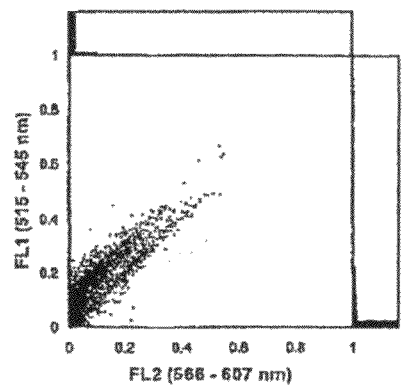
FIG. 2B is a fluorescence intensity scatter plot of FL1 intensity and FL2 intensity for a formulation with sucrose.
Figure 2C:
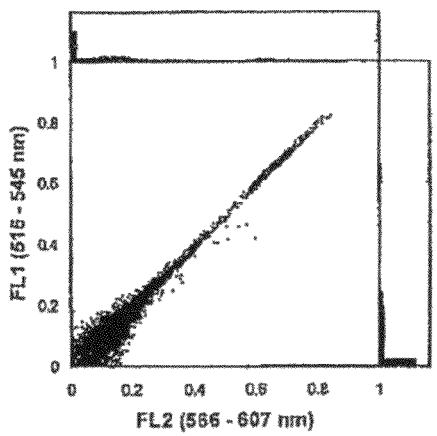
FIG. 2C is a fluorescence intensity scatter plot of FL1 intensity and FL2 intensity for a formulation with non-ionic surfactant.
Figure 2D:
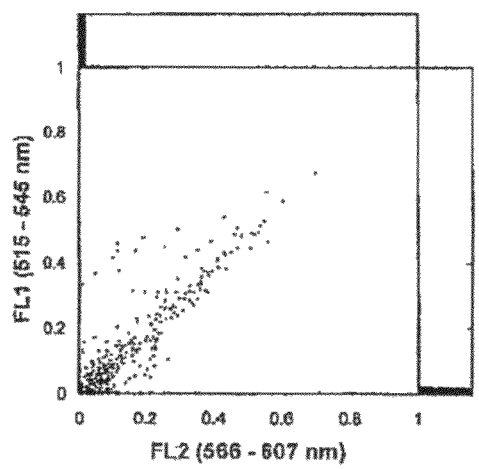
FIG. 2D is a fluorescence intensity scatter plot of FL1 intensity and FL2 intensity for a formulation with sucrose and non-ionic surfactant according to the present invention.

FIG. 2A shows particle intensities for a formulation containing only mAb and silicone oil. The scatter plot is linear across an order of magnitude in size (ca. 1-10 μm), indicating that the ratio of mAb concentration to silicone oil volume is constant for particles of different sizes. The addition of Tween 20® non-ionic surfactant (FIG. 2C) does not significantly affect FL1 or FL2 intensities. When sucrose is introduced to the formulation (right panels), ranges in fluorescence intensity are generally compressed. Moreover, the combined presence of sucrose and Tween 20® non-ionic surfactant greatly reduces mAb aggregation: more than half of the particles register negligible FL1 intensity (FIG. 2D). In FIG. 2B, multiple data trends suggest two or more distinct particle populations.

Deviations from linear in the scatter plot demonstrate that as oil droplets increase in size, regimes exist where particle growth in not linear. Instead, it appears that differences in surface roughness exist for particles of essentially the same size. While not intending to be bound by any theory, one plausible explanation of the non-linear, non-spherical particle growth is that particles grow by addition of smaller droplets without immediate coalescence. This "creaming" effect creates particles which are multi-droplet agglomerates. Fluorescence scanning allows measurement of antibody/oil contributions to particles as the particles agglomerate.

As particles grow in size (corresponding to an increase in red and green intensities) the ratio of antibody to oil remains generally constant. This supports the hypothesis that smaller oil droplets combine to form larger multi-droplet particles. It appears that antibody molecules absorbed to the surface of small silicone oil droplets remain associated with the silicone oil as droplets agglomerate to form larger particles.

Figure 3A:
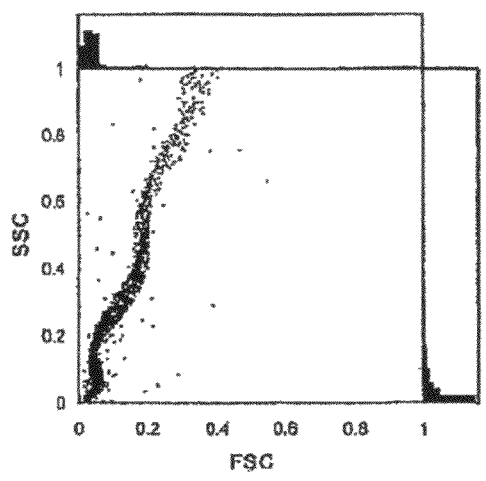
FIG. 3A is a scatter plot of side light scattering (90° light scattering) versus forward light scattering (180° light scattering) of silicone oil droplets for a control formulation without sucrose or surfactant.
Figure 3B:
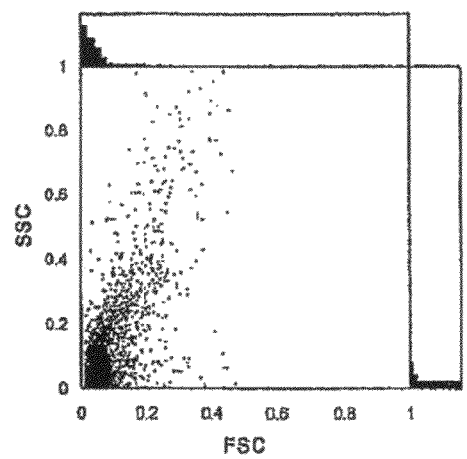
FIG. 3B is a scatter plot of side light scattering (90° light scattering) versus forward light scattering (180° light scattering) of silicone oil droplets for a formulation with sucrose.
Figure 3C:
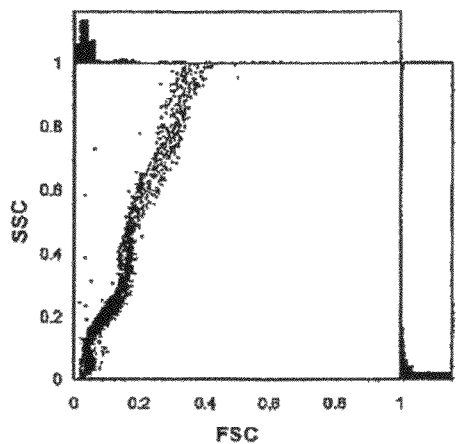
FIG. 3C is a scatter plot of side light scattering (90° light scattering) versus forward light scattering (180° light scattering) of silicone oil droplets for a formulation with non-ionic surfactant.
Figure 3D:
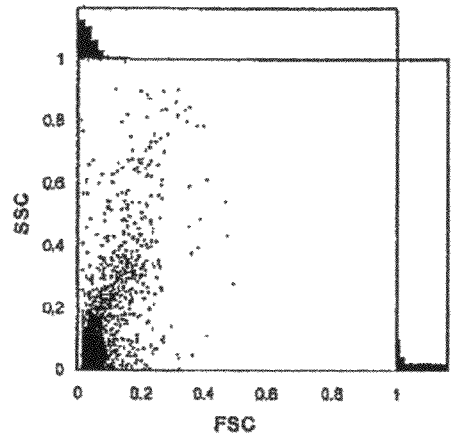
FIG. 3D is a scatter plot of side light scattering (90° light scattering) versus forward light scattering (180° light scattering) of silicone oil droplets for a formulation with non-ionic surfactant according to the present invention.

FIGS. 3A-3D are scatter plots of side light scattering (90° light scattering) versus forward light scattering (180° light scattering) of silicone oil droplets in aqueous mAb formulations (1 mg/mL) containing various combinations of sucrose and surfactants for the same four formulations A-D (see Table 1). Forward light scattering intensity is affected primarily by particle size, whereas side light scattering intensity is influenced by particle size and surface roughness. Axes units are arbitrary. Histograms represent particle distributions. Histogram scales range from 0 to 0.5. FIGS. 3A-3D depict formulations of 1 mg/mL mAb and silicone oil with various combinations of sucrose and surfactants: A neither sucrose nor surfactant, B 0.5 M sucrose, C 0.005% Tween 20® non-ionic surfactant, and D 0.5 M sucrose and 0.005% Tween 20® non-ionic surfactant. As shown in FIGS. 3B and 3D, the addition of sucrose greatly reduces average particle size (x-axis) and surface roughness (y-axis).

Figure 4A:
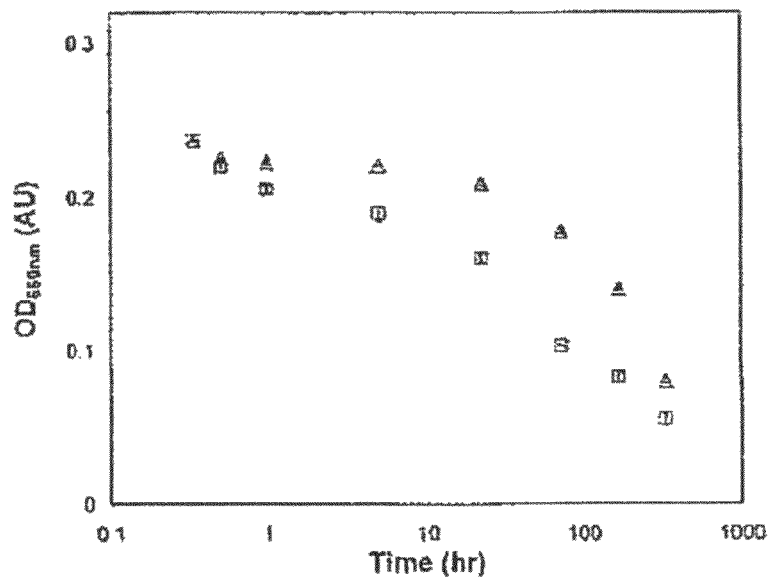
FIG. 4A is a plot of light obscuration as a function of time for a formulation including sucrose, mAb and silicone oil and a formulation including mAb and silicone oil.
Figure 4B:
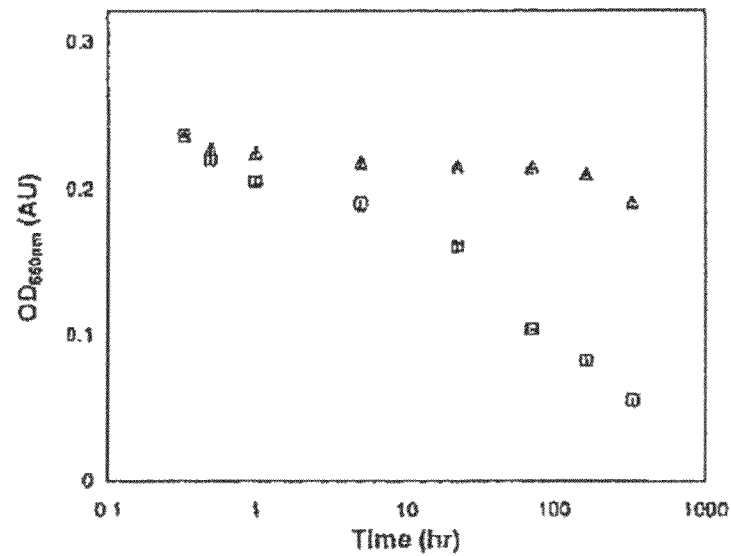
FIG. 4B is a plot of light obscuration as a function of time for a formulation including sucrose, mAb and silicone oil and a formulation including sucrose, non-ionic surfactant, mAb and silicone oil according to the present invention.

Relative rates of silicone oil coalescence are plotted in FIGS. 4A and 4B. FIGS. 4A and 4B show time dependence of light obscuration in mAb formulations with suspended silicone oil. Samples of each formulation were analyzed after brief swirling to deflocculate and de-cream suspensions. The initial time point of each formulation was normalized to the same value. Symbols are arithmetic means of three replicates and error bars represent ±1 standard deviation. In each of FIGS. 4A and 4B, mAb concentration is 1 mg/mL. In FIGS. 4A and 4B, squares denote formulations with 0.5 M sucrose, mAb, and silicone oil. In FIG. 4A, triangles denote formulations with only mAb and oil. FIG. 4A compares formulations of mAb and silicone oil with and without sucrose. As shown in FIG. 4A, sucrose enhanced the rate of silicone oil coalescence. In FIG. 4B, triangles denote formulations with 0.5 M sucrose, 0.005% Tween 20® non-ionic surfactant, mAb, and oil. FIG. 4B compares formulations with sucrose to formulations with sucrose and a non-ionic surfactant. As shown in FIG. 4B, Tween 20® non-ionic surfactants reduced silicone oil coalescence rates. Thus, suspended oil droplets remain in solution longer when Tween 20® non-ionic surfactant was present and shorter when sucrose was present.

Figure 5A:
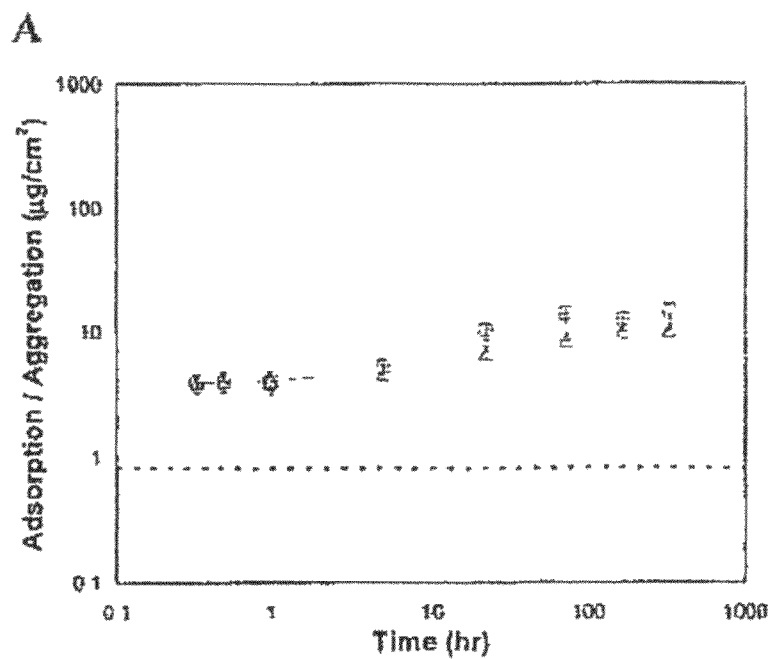
FIG. 5A is a plot of adsorption/aggregation of mAb with silicone oil as a function of time for a formulation including sucrose, mAb and silicone oil and a formulation including mAb and silicone oil.
Figure 5B:
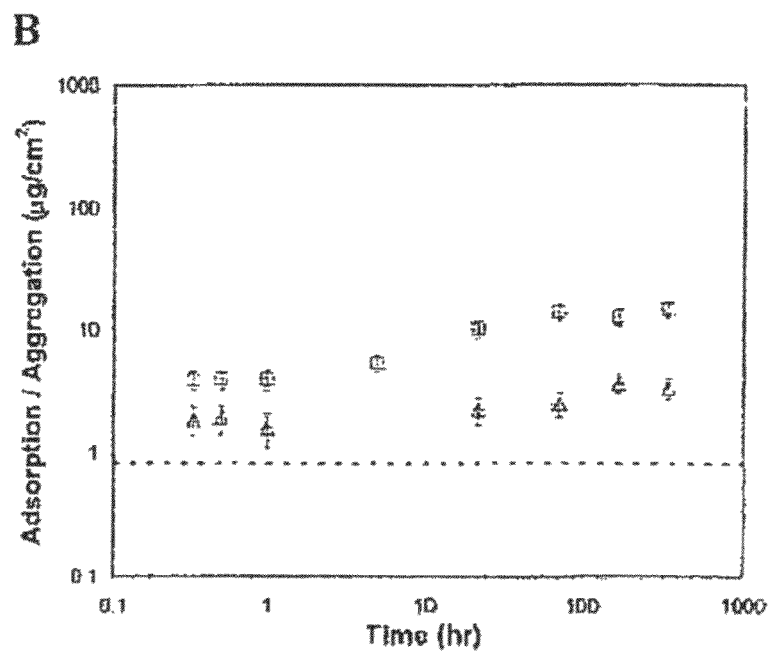
FIG. 5B is a plot of adsorption/aggregation of mAb with silicone oil as a function of time for a formulation including sucrose, mAb and silicone oil and a formulation including sucrose, non-ionic surfactant, mAb and silicone oil.

After estimating silicone oil surface area in each formulation at each time point, surface area normalized mAb aggregation can be calculated (FIGS. 5A-5B). Each of FIGS. 5A-5B corresponds to the same panel in FIG. 1, modified to account for silicone oil surface area. Symbols are arithmetic means of three replicates measured by difference between initial mAb concentration and mAb concentration in filtrate. Differences are divided by formulation- and time-specific silicone oil surface areas. Error bars represent ±1 standard deviation. In each of FIGS. 5A and 5B, mAb concentration is 1 mg/mL. In all panels, dashed lines represent an estimate of monolayer coverage and squares denote formulations with 0.5 M sucrose, mAb, and silicone oil. In FIG. 5A, triangles denote formulations with only mAb and oil. In FIG. 5B, triangles denote formulations with 0.5 M sucrose, 0.005% Tween 20® non-ionic surfactant, mAb, and oil. Normalized by silicone oil surface area, mAb aggregation actually increases in the presence of sucrose at sufficiently long times, as shown in FIG. 5A. In formulations containing sucrose and Tween 20® non-ionic surfactant, mAb/oil association levels remain low and relatively constant (FIG. 5B).

As shown in the above Figures, formulation additives can influence silicone oil droplet coalescence, levels of mAb exposure to silicone oil, and mAb aggregation. Moreover, combined effects of two or more formulation additives are sometimes more significant than the separate effects of each. Specifically, formulations containing both sucrose and Tween 20® non-ionic surfactant effectively reduce association of mAb with silicone oil, and addition of sucrose to formulations of markedly alters silicone oil droplet characteristics.

While not intending to be bound by any theory, the mechanism whereby sucrose reduces association of mAb with silicone oil is believed to be coalescence driven. In the above example, sucrose increases the rate of silicone oil coalescence, as shown in FIG. 4A. As droplets coalesce, total silicone oil surface area decreases. Because reduced surface area is available in formulations with sucrose, mAb aggregation rates decline at sufficiently long times (FIG. 1A). Interestingly, sucrose increases the extent of mAb/silicone oil association per silicone oil surface unit (FIG. 5A). Even so, overall aggregation rates improve due to enhanced coalescence. Thus, the addition of sucrose to therapeutic mAb formulations is beneficial not only for mAb stabilization, but potentially to reduce its exposure to silicone oil-surfaces.

The addition of Tween 20® non-ionic surfactant to formulations containing sucrose can further reduce mAb/oil association levels. This effect is especially evident at short times (FIG. 4B). Interestingly, Tween 20® non-ionic surfactant's effectiveness in inhibiting mAb/oil association is enhanced by the co-presence of sucrose, as shown in FIGS. 2C and 2D. In the absence of sucrose, fluorescence intensity scatter plots for formulations with Tween 20® non-ionic surfactant (FIG. 2C) do not significantly differ from those without Tween 20® non-ionic surfactant (FIG. 2A). However, when the sugar and non-ionic surfactant are both present in the formulation (FIG. 2D), reduction in mAb/oil association is enhanced.

The mechanism by which sucrose and Tween 20® non-ionic surfactant together prevent mAb aggregation differs from that of sucrose alone. As evidenced in FIG. 4B, the addition of Tween 20® non-ionic surfactant to formulations containing sucrose slows oil coalescence rates. From droplet size and number concentration measurements, suspended silicone oil surface area remains relatively constant up to 2 weeks after homogenization. Formulations with sucrose and Tween 20® non-ionic surfactant inhibit mAb aggregation, exhibiting nearly a factor of 2 reduction in aggregation over the next best formulation with sucrose but without Tween 20® non-ionic surfactant (FIG. 5B).

Because light scattering dot plots of silicone oil suspensions without mAb appear nearly identical to those shown in FIGS. 3 and 4, the scatter plot profiles primarily reveal information about silicone oil droplet characteristics, namely flocculation and coalescence. Sucrose-driven increases in silicone oil coalescence and creaming rates influence these dot plots. In formulations with sucrose, droplets are smaller, have less surface complexity, and have a tighter size range than in formulations without sucrose.

Figure 6:
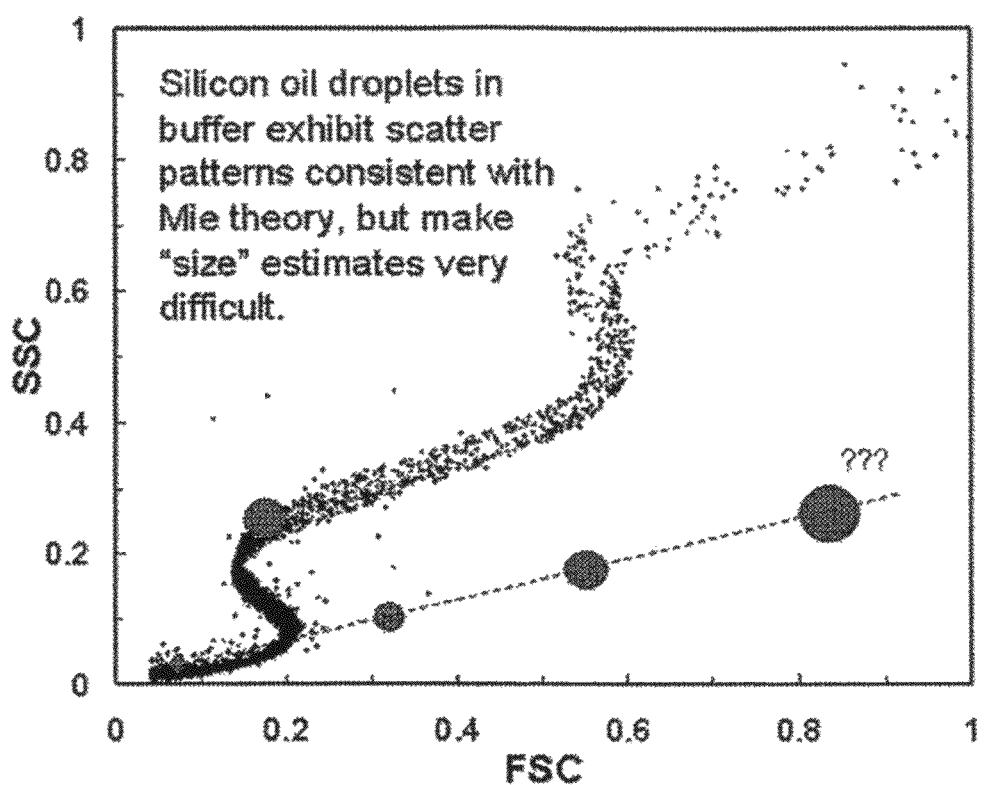
FIG. 6 is a hypothetical representation of silicone oil droplet and agglomerate distribution based on forward and side light scattering.

In formulations without sucrose in FIG. 3, the constrained data trends are of interest. Hypothetically, perfectly smooth spherical particles of varying size would create a linear trend, provided that perpendicular light scattering is optimally calibrated. Variations from linear indicate shape deviation from spherical. While not intending to be bound by any theory, it is believed that deviations observed in this study result from droplet flocculation without immediate coalescence. Thus, large particles composed of smaller spherical droplets exhibit surface complexity that does not exist with spherical particles. FIG. 6 is hypothetical representation of silicone oil droplet and agglomerate distribution based on forward and side light scattering. A linear trend (dotted line) would result from spherical droplets of varying diameter. Deviations from linear in the scatter plot profile can be explained by droplet agglomeration without immediate coalescence.

The presence of persistent agglomerates of droplets (i.e., floc which does not coalesce rapidly) may explain other phenomena observed in this investigation. Particle size distributions measured by laminar flow light obscuration (likely inducing de-flocculation) consistently revealed tighter ranges in droplet size than measurements by fluorescence activated particle scanning. Additionally, in many formulations without sucrose, the ratio of mAb concentration to silicone oil volume was relatively constant over a wide range in particle size. With slow coalescence, adsorbed mAb is not necessarily expelled from silicone oil surfaces upon flocculation. MAb concentration can then grow linearly with silicone oil agglomerate volume instead of surface area.

Divided trends in FL1 versus FL2 scatter plots can be explained by the presence of separate populations of particles. These trends occur in formulations with sucrose (FIG. 2B). Depending on formulation conditions, combinations of several particle populations may exist: mAb aggregates without silicone oil, mAb aggregates with a silicone oil nucleus, and silicone oil droplet agglomerates with mAb adsorbed to droplet surfaces. It is possible that hydrophobic pockets of mAb aggregates strip Nile Red dye from silicone oil. Alternately, a silicone oil droplet could act as a nucleus for mAb aggregation.

Therapeutic mAb formulations containing sucrose and Tween 20® non-ionic surfactant notably reduce mAb aggregation in the presence of silicone oil. To a smaller extent, formulations with only sucrose reduce mAb aggregation, likely due to increased silicone oil coalescence rates. Because silicone oil contamination has been shown to induce protein aggregation, successful formulation strategies to reduce protein aggregation can be important for products exposed to silicone oil. The addition of sucrose to therapeutic protein formulations may reduce protein exposure to silicone oil surfaces. As shown in the above Example, formulations containing sucrose and a non-ionic surfactant can inhibit silicone oil induced protein aggregation.

Example B

Effect of Oil Viscosity on Oil Loading in Suspension

Figure 7:
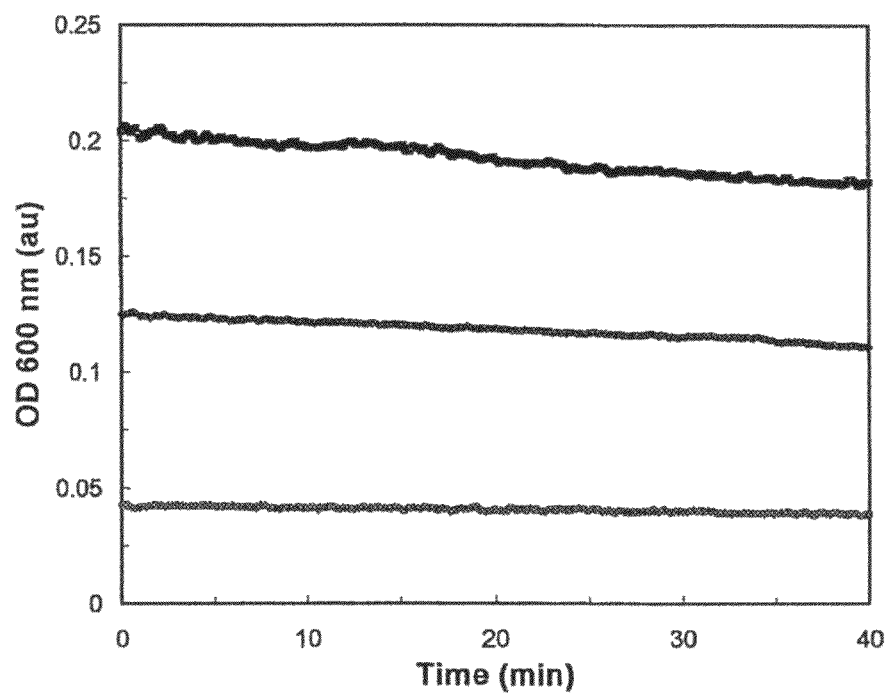
FIG. 7 is a plot of light obscuration as a function of time for silicone oil emulsion formulations for three different silicone oil viscosities.
Figure 8:
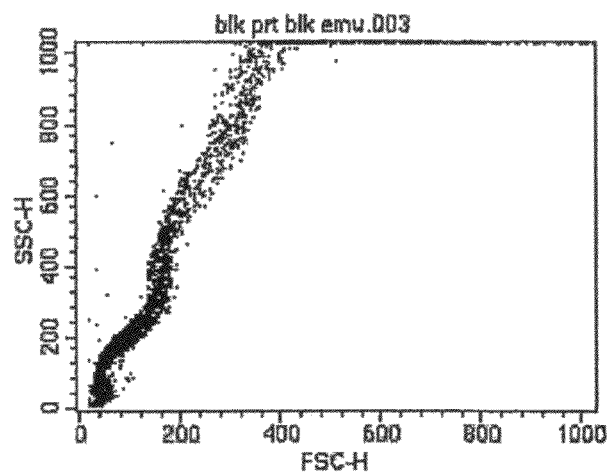
FIG. 8 is a scatter plot of side light scattering (90° light scattering) versus forward light scattering (180° light scattering) of silicone oil droplets for a formulation prepared from 1000 cSt silicone oil.
Figure 9:
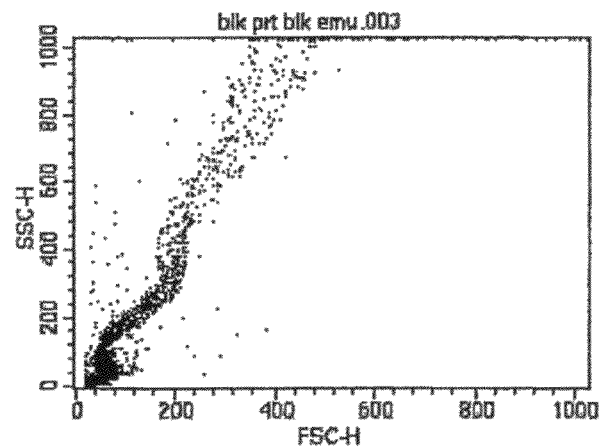
FIG. 9 is a scatter plot of side light scattering (90° light scattering) versus forward light scattering (180° light scattering) of silicone oil droplets for a formulation prepared from 12,500 cSt silicone oil.

Medical grade silicone oil was added to aqueous solutions with and without non-ionic surfactant as shown in Table 2. Concentration and viscosity of silicone oil in each sample is set forth in Table 2 below. FIG. 7 shows the influence of oil viscosity on oil loading indirectly by measurement of optical density at 600 nm. Optical density at 600 nm ($OD_{600}$) is an indirect measure of suspended oil concentration. As shown in FIG. 7 and Table 2, lower oil viscosity reflects higher initial $OD_{600}$, which in turn permits higher oil loading. As shown in FIGS. 8 and 9, there was no qualitative difference in coalescence behavior of suspended oil droplets of differing viscosity (1,000 cSt vs. 12,500 cSt) polydimethylsiloxane for the samples tested.

TABLE 2

| Oil Type ($c_{oil} = 0.5\%$) | Initial $OD_{600}$ (au) |
|---|---|
| 350 cSt | 0.21 |
| 1000 cSt | 0.12 |
| 12500 cSt | 0.04 |
| 350 cSt 0.1% Tween 20 ® | 0.53 |
| 1000 cSt 0.1% Tween 20 ® | 0.13 |
| 12500 cSt 0.1% Tween 20 ® | 0.16 |

Example C

Silicone oil was labeled as described above in Example A by dissolving Nile Red dye in silicone oil at 5 mg/ml. The monoclonal antibody used in the study was the standard commercially available Pacific Blue® Mouse Anti-human CD4 mAb (clone RPA-T4, Becton, Dickinson and Company). Pacific Blue® dye has an emission maximum of 455 nm. Nile Red dye has an emission maximum of 628 nm, however significant Nile Red emission signal occurs in the detector normally used for R-phycoerythrin (PE), and was the emission detector used for Nile Red-labeled samples for this Example C. Suspensions with Pacific Blue® labeled mAb and Nile Red-labeled silicone oil were prepared as described above in Example A and analyzed with a BD™ LSR II Flow Cytometer analyzer (Becton, Dickinson and Company) using violet laser excitation (405 nm) for Pacific Blue® detection (450/50 BP filter) and blue laser excitation (488 nm) for Nile Red detection (585/42 BP filter). All fluorescence measurements were done using pulse area to insure total fluorescence was measured for each particle. To properly show fluorescence distributions over a wide dynamic range (4 decades) yet allow zero and negative values to be properly displayed, the biexponential transformation (Logicle, D R Parks, W A Moore, Stanford University) was used from within BD Diva Software.

The degree to which the labeled CD3 antibody interacts with silicone oil droplets in suspension depends on the formulation environment and incubation time. FIGS. 12A-12D illustrate the association of mAb with both unlabeled silicone oil and silicon oil labeled with Nile Red. In all samples containing mAb, the mAb concentration was 2 μg/ml.

Referring now to FIGS. 13A and 13B, the slope of the Pacific Blue® signal from the labeled mAb as a function of the Nile Red signal (FIG. 13B) was very near that of the ideal theoretical for surface area as a function of volume (FIG. 13A). In theory, for a perfect sphere the slope of surface area to volume is 10 to the two thirds power ($10^{0.667}$), and the observed slope was $10^{0.603}$, in agreement with the expectation that the mAb is present on the exterior of the oil droplets or particle as opposed to being captured or distributed within the interior of the oil particle. If the mAb were distributed in a linear manner with the Nile Red labeled oil droplets, the slope would be near 1.0 on either a logarithmic plot or on the logarithmic portion of a biexponential display.

The effect of non-ionic surfactant on separation of silicone oil particles from mAb particles and agglomerates of silicone oil and mAb particles is shown in FIGS. 14A and 14B. FIG. 14A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention. FIG. 14B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween, 20® polyoxyethylene 20 sorbitan monolaurate non-ionic surfactant according to the present invention. After digital baseline correction, the relative fluorescence values essentially amount to scores and indicate the signal strength, with populations having no detectable signal having a central tendency near zero with half the values negative and half the values positive. The biexponential transformation is a variance normalizing transformation that permits zero and negative values to be displayed at the low end of the scale based upon the variance of the dimmest population, smooth transition to log, and the majority of the display range equivalent to a standard log scale. As shown in FIG. 14B, Tween 20® non-ionic surfactant is effective in inhibiting mAb/oil association.

Figure 15A:
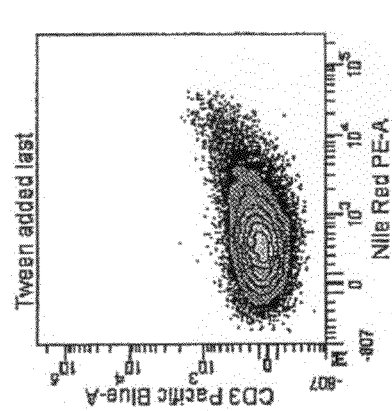
FIG. 15A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention.
Figure 15B:
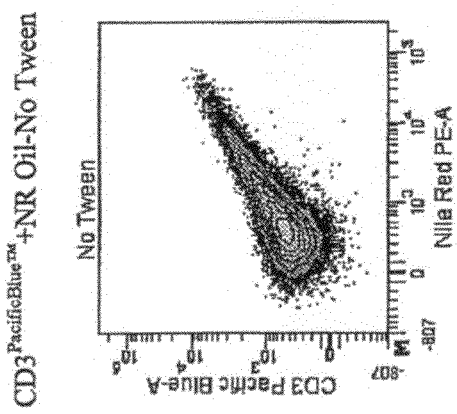
FIG. 15B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant according to the present invention.

The effect of non-ionic surfactant on separation of silicone oil particles from mAb particles and agglomerates of silicone oil and mAb particles is shown in FIGS. 15A and 15B. FIG. 15A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention. FIG. 15B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant according to the present invention added after exposing the labeled protein to the oil droplet. As shown in FIG. 15B, Tween 20® non-ionic surfactant is effective in inhibiting mAb/oil association.

The effects of non-ionic surfactant, salt and sugar on separation of silicone oil particles from mAb particles and agglomerates of silicone oil and mAb particles is shown in FIGS. 16A-16D. FIG. 16A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye according to the present invention. FIG. 16B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 150 mM NaCl salt according to the present invention. As shown by comparison of FIGS. 16A (formulation without salt) and 16B (formulation with salt), the presence of NaCl salt did not appear to inhibit mAb/oil association.

FIG. 16C is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.5 M sucrose according to the present invention. As shown by comparison of FIGS. 16A (formulation without sucrose) and 16C (formulation with sucrose), the presence of sucrose did not appear to inhibit mAb/oil association.

FIG. 16D is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, 0.5 M sucrose, 150 mM Salt, and 0.03% Tween, 20® polyoxyethylene 20 sorbitan monolaurate non-ionic surfactant according to the present invention. As shown by comparison of FIGS. 16A (formulation without salt, sucrose or non-ionic surfactant) and 16D (formulation with salt, sucrose and Tween 20® non-ionic surfactant), the presence of salt, sucrose and Tween 20® non-ionic surfactant inhibited mAb/oil association.

In fluorescence activated particle scanning, the electronic pulse window is the timing window (window gate) which allows signals to be processed within a specified frame of time. Usually this is set at a conservative constant value (according to the manufacturer's instructions for a particular instrument, often several microseconds longer than minimally required) during data acquisition to ensure complete integration of the pulses. The effect of decreasing the time to only that required to completely integrate the signals on a finely calibrated system (by adjusting the window extension) was evaluated at 10 µs vs. 2 µs for samples with and without non-ionic surfactant. FIG. 17A is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye measured at a window extension of 10 us according to the present invention. FIG. 17B is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant measured at a window extension of 10 µs according to the present invention. FIG. 17C is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye and CD3 antibody labeled with Pacific Blue™ dye measured at a window extension of 2 µs according to the present invention. FIG. 17D is a plot of relative fluorescence intensity of CD3 antibody labeled with Pacific Blue™ dye (y-axis) versus relative fluorescence intensity of Nile Red labeled silicone oil (x-axis) for a sample of silicone oil labeled with Nile Red dye, CD3 antibody labeled with Pacific Blue™ dye, and 0.03% Tween 20® polyoxyethylene 20 sorbitan monolaurate non-ionic surfactant measured at a window extension of 2 µs according to the present invention. As shown by comparison of FIGS. 17A and 17C, and FIGS. 17B and 17D, respectively, decreasing the window extension from 10 μs to 2 μs reduces the population coefficient of variation (CV) in both dye dimensions.

The present invention has been described with reference to specific details of particular embodiments thereof. It is not intended that such details be regarded as limitations upon the scope of the invention except insofar as and to the extent that they are included in the accompanying claims.

What is claimed is:

1. A method for evaluating the aggregation of a proteinaceous material in a suspension comprising an organopolysiloxane, comprising:
    (a) providing an aqueous suspension of a fluorescently-labeled organopolysiloxane and a fluorescently-labeled proteinaceous material;
    (b) measuring relative particle fluorescence intensity of the fluorescently-labeled organopolysiloxane and the fluorescently-labeled proteinaceous material using fluorescence-activated particle sorting; and
    (c) evaluating the aggregation of the proteinaceous material by comparing the relative intensity of the fluorescently-labeled organopolysiloxane to the relative intensity of the fluorescently-labeled proteinaceous material, wherein the relative intensity of the fluorescently-labeled organopolysiloxane as compared to the relative intensity of the fluorescently-labeled proteinaceous material indicates the aggregation of the proteinaceous material.

2. The method according to claim 1, wherein the fluorescently-labeled proteinaceous material comprises at least one proteinaceous material which is a monoclonal antibody.

3. The method according to claim 2, wherein the monoclonal antibody is selected from the group consisting of infliximab, basiliximab, abciximab, daclizumab, gemtuzumab, alemtuzumab, rituximab, palivizumab, trastuzumab and etanercept.

4. The method according to claim 1, wherein the organopolysiloxane is labeled with a first fluorescent moiety which emits light within a first range of wavelengths and the proteinaceous material is labeled with a second fluorescent moiety which emits light within a second range of wavelengths when the first fluorescent moiety and the second fluorescent moiety are each exposed to light of the same wavelength emitted by a laser, wherein the first range of wavelengths is substantially free of overlap with the second range of wavelengths.

5. The method according to claim 4, wherein the first range of wavelengths overlap with the second range of wavelengths less than 5% on a basis of total combined normalized range of wavelengths of the first range of wavelengths and the second range of wavelengths.

6. The method according to claim 1, wherein the organopolysiloxane is labeled with Nile Red fluorescent moiety which emits undetectable levels of light over a range of 450 nm to 650 nm and the proteinaceous material is labeled with Pacific Blue dye which emits light over a range of 340 nm to 450 nm when exposed to a 405 nm violet laser.

7. The method according to claim 1, wherein the aqueous suspension further comprises at least one non-ionic surfactant.

8. The method according to claim 7, wherein the non-ionic surfactant is selected from the group consisting of acetylenic glycols, alkanolamides, alkanolamines, alkyl phenols, fatty acids, fatty alcohols, fatty esters, glycerol esters, monododecyl ethers, phenol derivatives, poloxamers, poloxamines, polyoxyethylene acyl ethers, polyoxyethyleneglycol dodecyl ethers, sodium dodecyl sulfates, sorbitols, sorbitan derivatives and mixtures thereof.

9. The method according to claim 8, wherein the non-ionic surfactant is a sorbitan derivative selected from the group consisting of sorbitan fatty acid esters, polyoxyethylene sorbitan fatty acid esters and mixtures thereof.

10. The method according to claim 1, wherein the aqueous suspension further comprises at least one sugar.

11. The method according to claim 7, wherein the aqueous suspension further comprises at least one sugar.

12. The method according to claim 10, wherein the sugar is selected from the group consisting of monosaccharides, disaccharides, trisaccharides, oligosaccharides and mixtures thereof.

13. The method according to claim 12, wherein the sugar is selected from the group consisting of sucrose, lactose, fructose, glucose, galactose, mannose, mannose and mixtures thereof.

14. The method according to claim 9, wherein the non-ionic surfactant is a polyoxyethylene sorbitan fatty acid ester and further comprising a sugar which is sucrose.

15. The method according to claim 1, further comprising providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein a concentration of the at least one aggregation inhibitor is different in each aqueous suspension, measuring relative particle fluorescence intensity of the fluorescently-labeled organopolysiloxane and the fluorescently-labeled proteinaceous material in each aqueous suspension using fluorescence-activated particle sorting; and comparing the relative intensity of the fluorescently-labeled organopolysiloxane to the relative intensity of the fluorescently-labeled proteinaceous material for each aqueous suspension.

16. The method according to claim 1, further comprising providing a plurality of aqueous suspensions of a fluorescently-labeled organopolysiloxane and a fluorescently-labeled proteinaceous material, wherein each aqueous suspension further comprises at least one aggregation inhibitor selected from the group consisting of non-ionic surfactants and sugars wherein the at least one aggregation inhibitor is different in each aqueous suspension, measuring relative particle fluorescence intensity of the fluorescently-labeled organopolysiloxane and the fluorescently-labeled proteinaceous material in each aqueous suspension using fluorescence-activated particle sorting; and comparing the relative intensity of the fluorescently-labeled organopolysiloxane to the relative intensity of the fluorescently-labeled proteinaceous material for each aqueous suspension.

17. The method according to claim 15, further comprising selecting at least one aggregation inhibitor for use in a suspension comprising a proteinaceous material based upon the comparison of the relative intensity of the fluorescently-labeled organopolysiloxane to the relative intensity of the fluorescently-labeled proteinaceous material for each aqueous suspension.

18. The method of claim 1, in which the relative particle fluorescence intensity of the fluorescently-labeled organopolysiloxane and the fluorescently-labeled proteinaceous material using fluorescence-activated particle sorting is measured in a flow cytometer and aggregation is evaluated from data output of the flow cytometer.

19. The method of claim 18, in which light scattering data for the particles is measured and the aggregation of the light scattering data is used with fluorescent intensity data to produce an output.

* * * * *

UNITED STATES PATENT AND TRADEMARK OFFICE
CERTIFICATE OF CORRECTION

PATENT NO. : 8,633,034 B2  Page 1 of 1
APPLICATION NO. : 12/739009
DATED : January 21, 2014
INVENTOR(S) : Trotter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Twenty-second Day of September, 2015

Michelle K. Lee
*Director of the United States Patent and Trademark Office*